US008155892B2

(12) United States Patent
Nassif et al.

(10) Patent No.: US 8,155,892 B2
(45) Date of Patent: Apr. 10, 2012

(54) MEANS FOR IDENTIFYING A STRAIN ISOLATED FROM A CLINICAL SAMPLE AT THE SPECIES AND/OR SUBSPECIES LEVEL

(75) Inventors: Xavier Nassif, Paris (FR); Jean-Luc Beretti, Les Clayes sous Bois (FR); Etienne Carbonnelle, Paris (FR); Agnès Ferroni, Clamart (FR); Marie Elisabeth Bougnoux, Malakoff (FR); Nicolas Degand, Paris (FR); Alexandre Alanio, Paris (FR)

(73) Assignees: Assistance Publique-Hopitaux de Paris (APHP), Paris Cedex (FR); Universite Paris Descartes, Paris Cedex (FR)

( * ) Notice: Subject to any disclaimer, the term of this patent is extended or adjusted under 35 U.S.C. 154(b) by 107 days.

(21) Appl. No.: 12/458,353

(22) Filed: Jul. 8, 2009

(65) Prior Publication Data
US 2010/0116980 A1 May 13, 2010

Related U.S. Application Data

(63) Continuation-in-part of application No. PCT/IB2008/001058, filed on Jan. 8, 2008.

(30) Foreign Application Priority Data

Jan. 8, 2007 (EP) ..................................... 07290019

(51) Int. Cl.
*G06F 19/00* (2011.01)

(52) U.S. Cl. .............................. 702/27; 435/6; 435/91.1

(58) Field of Classification Search .................. 250/282; 435/6, 91.1, 91.2; 536/23.1, 23.5, 24.3; 702/27
See application file for complete search history.

(56) References Cited

U.S. PATENT DOCUMENTS

| 6,177,266 | B1 | 1/2001 | Krishnamurthy et al. |
| 7,020,559 | B1 | 3/2006 | Demirev et al. |
| 7,122,644 | B2 * | 10/2006 | Yen-Potin et al. ........... 536/23.1 |
| 7,427,482 | B2 * | 9/2008 | Blumenfeld et al. ............. 435/6 |
| 2002/0192676 | A1 | 12/2002 | Madonna et al. |

FOREIGN PATENT DOCUMENTS

| DE | 10 2005 002672 | 7/2006 |
| WO | WO 98/09314 | 3/1998 |
| WO | WO 01/92872 | 12/2001 |

OTHER PUBLICATIONS

International Search Report for PCT/IB2008/001058, mailed Aug. 21, 2008.
Written Opinion of the International Searching Authority for PCT/IB2008/001058, mailed Aug. 21, 2008.
Dare, D., "Rapid Bacterial Characterization and Identification by MALDI-TOF Mass Spectrometry", Advanced Techniques in Diagnositic Microbiology, (Jun. 16, 2006), pp. 117-133.

(Continued)

Primary Examiner — Kiet T Nguyen
(74) Attorney, Agent, or Firm — Nixon & Vanderhye P.C.

(57) ABSTRACT

The invention relates to a method for identifying a strain isolated from a clinical sample, at the species and/or subspecies level, using MALDI-TOF-MS analysis comprising a step of classifying the germ in a group before performing the MALDI-TOF-MS analysis.

20 Claims, 19 Drawing Sheets

OTHER PUBLICATIONS

Figure 1:
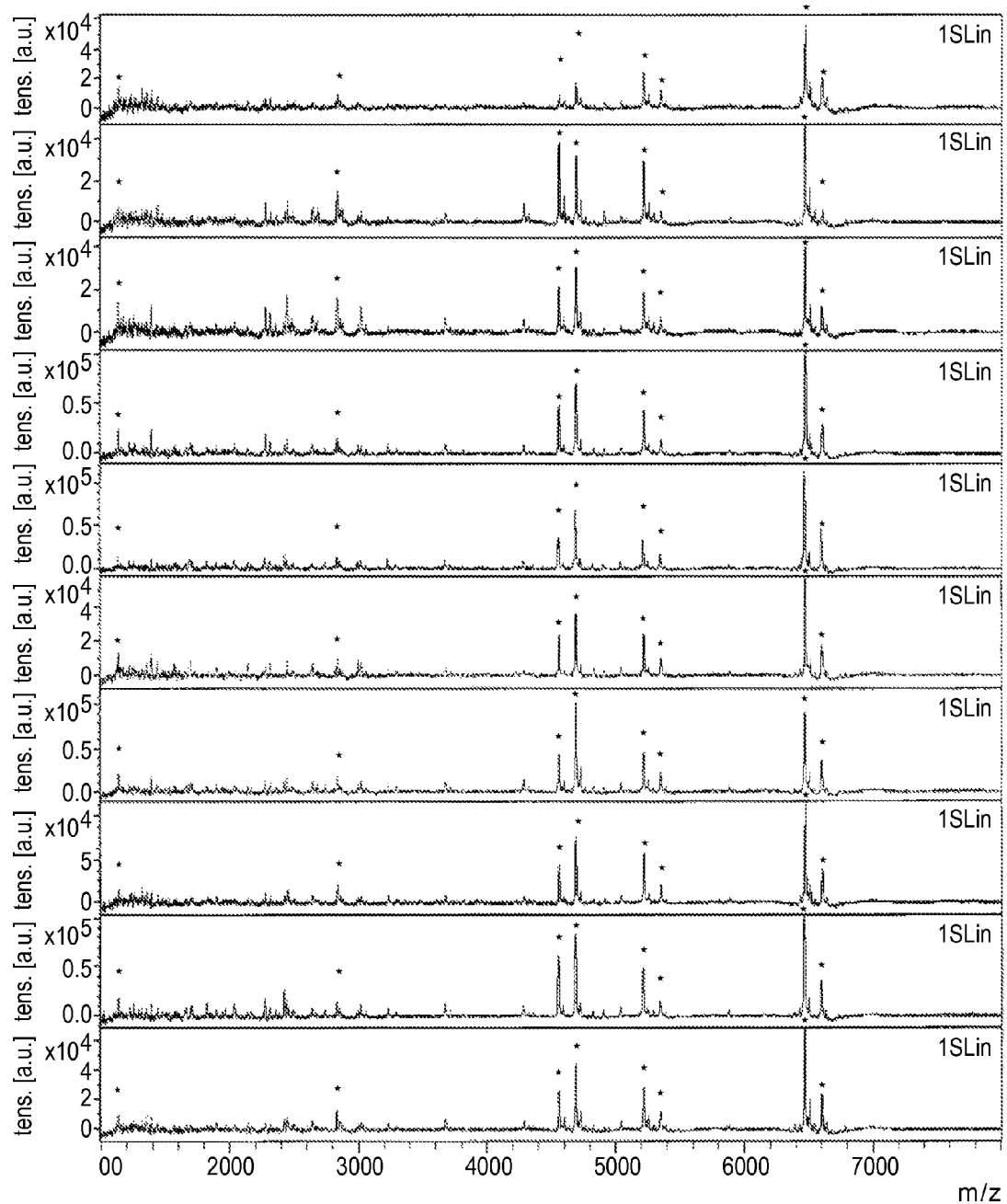

Du, Z. et al., "Identification of *Staphylococcus aureus* and Determination of Its Methicillin Resistance by Matrix-Assisted Laser Desorption/Ionization Time-Of-Flight Mass Spectrometry", Analytical Chemistry, vol. 74, No. 21, (Nov. 1, 2002), pp. 5487-5491.

Walker, J. et al., "Intact Cell Mass Spectrometry (ICMS) used to Type Methicillin-Resistant *Staphylococcus aureus*: Media Effects and Inter-Laboratory Reproducibility", Journal of Microbiological Methods, vol. 48, No. 2-3, (Feb. 2002), pp. 117-126.

Smole, S.C. et al., "Sample. Preparation of Gram-Positive Bacteria for Identification by Matrix Assisted Laser Desorption/Ionization Time-of-Flight.", Journal of Microbiological Methods, vol. 48, No. 2-3, (Feb. 2002), pp. 107-115.

Keys, C.J. et al., "Compilation of a MALDI-TOF Mass Spectral Database for the Rapid Screening and Characterisation of Bacteria Implicated in Human Infectious Diseases", Infection Genetics and Evolution, vol. 4, No. 3, (Sep. 2004), pp. 221-242.

Coales, M.C. et al., "Characterisation of the *Staphylococcus sciuri* Group by Matrix-Assisted Laser Desorption/Ionisation Time-of-Flight Mass Spectrometry", Abstracts of the General Meeting of the American Society for Microbiology, vol. 102, (May 19-23, 2002), pp. 103.

Nagai R. et al., "Rapid Species Level Identification of Coagulase Negative *Staphylococcal* Strains from revision Joint Replacement Operations by Intact Cell Mass Spectrometry", J. Bone Joint Surg Br Proceedings, vol. 88-B, (May 2006), pp. 238.

Nielsen, P.B. et al., "Matrix-Assisted Laser Desorption/Ionisation Time-of-Flight Mass Spectrometry Provides Fast and Reliable Identification of *Staphylococcus haemolyticus*", Clinical Microbiology and Infection, vol. 11, No. Supple-2, (2005), p. 210.

\* cited by examiner

FIGURE 3-1

| | database 1 | database 2 | database 3 | database 4 | | database 1 | database 2 | database 3 | database 4 |
|---|---|---|---|---|---|---|---|---|---|
| S.aureus | 2196 (+/-2)<br>2234 (+/-2)<br>2284 (+/-2)<br>2302 (+/-2)<br>2323 (+/-2)<br>2342 (+/-2)<br>3005 (+/-2)<br>3043 (+/-2)<br>4526 (+/-2)<br>5509 (+/-2)<br>6893 (+/-2) | 2194 (+/-2)<br>2217 (+/-2)<br>2233 (+/-2)<br>2282 (+/-2)<br>2302 (+/-3)<br>2340 (+/-3)<br>2680 (+/-3)<br>2719 (+/-3)<br>3004 (+/-3)<br>3042 (+/-3)<br>6891 (+/-4) | 1696 (+/-2)<br>1788 (+/-2)<br>3007 (+/-2)<br>4307 (+/-2)<br>5035 (+/-2)<br>5510 (+/-2)<br>6892 (+/-2) | 1785 (+/-2)<br>2682 (+/-2)<br>2976 (+/-2)<br>3005 (+/-2)<br>3041 (+/-3)<br>5512 (+/-3)<br>6825 (+/-5)<br>6896 (+/-5) | S.intermedius | 2092 (+/-2)<br>2117 (+/-1)<br>2133 (+/-1)<br>2154 (+/-1)<br>2170 (+/-2)<br>4278 (+/-3)<br>4796 (+/-3)<br>6244 (+/-4)<br>6732 (+/-4)<br>6770 (+/-5) | 1358 (+/-3)<br>2092 (+/-2)<br>2117 (+/-2)<br>2133 (+/-2)<br>2154 (+/-2)<br>2777 (+/-2)<br>2816 (+/-2)<br>4278 (+/-1)<br>4796 (+/-2)<br>6244 (+/-3)<br>6733 (+/-3)<br>6771 (+/-3) | 1378 (+/-2)<br>2094 (+/-2)<br>2135 (+/-2)<br>4279 (+/-2)<br>4797 (+/-2)<br>6245 (+/-2)<br>6733 (+/-2) | 2133 (+/-2)<br>4278 (+/-2)<br>4796 (+/-3)<br>6245 (+/-5)<br>6734 (+/-5)<br>6873 (+/-5) |
| S.capitis capitis | 2611 (+/-2)<br>2642 (+/-2)<br>2664 (+/-2)<br>2681 (+/-2)<br>2908 (+/-2)<br>2947 (+/-2)<br>5099 (+/-3)<br>6713 (+/-4) | 2446 (+/-2)<br>2610 (+/-2)<br>2642 (+/-2)<br>2664 (+/-2)<br>2680 (+/-2)<br>2702 (+/-2)<br>2719 (+/-2)<br>2908 (+/-2)<br>2946 (+/-1)<br>5071 (+/-2)<br>5098 (+/-2)<br>5136 (+/-3)<br>6713 (+/-4)<br>6748 (+/-1) | 2613 (+/-2)<br>2645 (+/-2)<br>5101 (+/-2)<br>6715 (+/-2) | 2446 (+/-3)<br>2483 (+/-2)<br>2611 (+/-3)<br>2908 (+/-3)<br>5100 (+/-4)<br>6716 (+/-6) | S.lugdunensis | 2586 (+/-2)<br>2744 (+/-2)<br>2782 (+/-2)<br>3078 (+/-2)<br>4460 (+/-3)<br>4499 (+/-3)<br>4568 (+/-3)<br>4953 (+/-3)<br>5166 (+/-4) | 2547 (+/-2)<br>2586 (+/-2)<br>2743 (+/-2)<br>2764 (+/-3)<br>2781 (+/-2)<br>4949 (+/-2)<br>5162 (+/-2)<br>5183 (+/-2)<br>5200 (+/-2)<br>5238 (+/-2)<br>5298 (+/-2)<br>7351 (+/-3) | 2549 (+/-2)<br>2745 (+/-2)<br>4953 (+/-3)<br>5166 (+/-3)<br>7357 (+/-4) | 2546 (+/-1)<br>2585 (+/-1)<br>2742 (+/-1)<br>4955 (+/-3)<br>5152 (+/-3)<br>5167 (+/-4)<br>5206 (+/-4)<br>5304 (+/-4)<br>7363 (+/-5) |
| S.capitis ureolyticus | 5098 (+/-3)<br>5137 (+/-3)<br>5235 (+/-3)<br>6713 (+/-4)<br>6751 (+/-4) | 2580 (+/-2)<br>5041 (+/-3)<br>5082 (+/-3)<br>5098 (+/-2)<br>5120 (+/-2)<br>5136 (+/-2) | 5084 (+/-2)<br>5100 (+/-2)<br>5122 (+/-2)<br>5139 (+/-2)<br>5236 (+/-2)<br>6715 (+/-2) | 5100 (+/-3)<br>5138 (+/-3)<br>5236 (+/-3)<br>6717 (+/-5) | S.pasteuri | 2176 (+/-1)<br>2215 (+/-1)<br>2352 (+/-2)<br>2393 (+/-2)<br>2432 (+/-2)<br>2784 (+/-2) | 2176 (+/-2)<br>2215 (+/-2)<br>2352 (+/-2)<br>2375 (+/-2)<br>2393 (+/-2)<br>2433 (+/-2) | 2178 (+/-2)<br>2353 (+/-2)<br>2395 (+/-2)<br>2434 (+/-2)<br>2786 (+/-2)<br>2808 (+/-2) | 2176 (+/-3)<br>2352 (+/-3)<br>2394 (+/-3)<br>2785 (+/-3)<br>2806 (+/-2)<br>2824 (+/-3) |

FIGURE 3-2

| | | | | | | | |
|---|---|---|---|---|---|---|---|
| S.caprae | 2642 (+/-1)<br>2665 (+/-1)<br>2681 (+/-1)<br>2959 (+/-1)<br>4481 (+/-2)<br>6567 (+/-4) | | | 5235 (+/-3)<br>6713 (+/-4)<br>6752 (+/-4) | 2807 (+/-2)<br>2823 (+/-2)<br>2866 (+/-2)<br>2888 (+/-2)<br>2905 (+/-2) | 2785 (+/-2)<br>2807 (+/-2)<br>2824 (+/-2)<br>2866 (+/-2)<br>2889 (+/-2)<br>2905 (+/-2) | 2825 (+/-3)<br>2867 (+/-3)<br>2889 (+/-3)<br>2906 (+/-3) | 2867 (+/-3)<br>2888 (+/-2)<br>2904 (+/-2)<br>4531 (+/-4)<br>4965 (+/-4)<br>6182 (+/-5) |
| S.saprophyticus bovis | | 2921 (+/-2)<br>2956 (+/-3)<br>5016 (+/-2)<br>5216 (+/-2)<br>5254 (+/-2)<br>7050 (+/-2) | 2554 (+/-2)<br>2920 (+/-2)<br>2957 (+/-3)<br>5017 (+/-3)<br>5217 (+/-4)<br>7052 (+/-6) | 1004 (+/-2)<br>2553 (+/-2)<br>2641 (+/-2)<br>2664 (+/-2)<br>2680 (+/-2)<br>2702 (+/-2)<br>2718 (+/-2)<br>2740 (+/-2)<br>2920 (+/-2)<br>2954 (+/-5)<br>5214 (+/-2)<br>5252 (+/-3) | 2478 (+/-2)<br>2499 (+/-2)<br>2517 (+/-2)<br>2828 (+/-3)<br>4936 (+/-4)<br>4987 (+/-3)<br>6288 (+/-2)<br>6383 (+/-5)<br>6617 (+/-5) | 1004 (+/-2)<br>2478 (+/-2)<br>2497 (+/-4)<br>2517 (+/-2)<br>4263 (+/-3)<br>4936 (+/-3)<br>4987 (+/-3)<br>6037 (+/-3)<br>6289 (+/-4)<br>6384 (+/-4)<br>6394 (+/-4)<br>6618 (+/-4) | 1118 (+/-2)<br>1144 (+/-3)<br>1158 (+/-2)<br>4265 (+/-3)<br>6291 (+/-3)<br>6386 (+/-3)<br>6399 (+/-4) | 3761 (+/-1)<br>4262 (+/-2)<br>6290 (+/-4)<br>6385 (+/-4)<br>6619 (+/-4) |
| S.cohni cohni | 2074 (+/-1)<br>2097 (+/-1)<br>2113 (+/-1)<br>2690 (+/-1)<br>4481 (+/-2)<br>6567 (+/-4) | 1095 (+/-2)<br>1118 (+/-2)<br>1132 (+/-2)<br>1146 (+/-2)<br>1416 (+/-2)<br>2077 (+/-3)<br>2115 (+/-3)<br>2181 (+/-3)<br>2192 (+/-2)<br>2406 (+/-2) | 1003 (+/-3)<br>2073 (+/-1)<br>2096 (+/-1)<br>2112 (+/-2)<br>2401 (+/-3)<br>2440 (+/-2)<br>2688 (+/-2)<br>4457 (+/-3)<br>4484 (+/-2)<br>4910 (+/-2)<br>5821 (+/-4) | 1370 (+/-2)<br>2073 (+/-2)<br>2096 (+/-2)<br>2112 (+/-1)<br>2135 (+/-1)<br>2401 (+/-2)<br>2689 (+/-1)<br>4480 (+/-0)<br>5817 (+/-1) | S.saprophyticus saprophyticus | 1004 (+/-1)<br>2478 (+/-2)<br>2828 (+/-2)<br>4935 (+/-4)<br>4986 (+/-4)<br>5066 (+/-4)<br>6228 (+/-5)<br>6617 (+/-5) | 1004 (+/-2)<br>2126 (+/-2)<br>2479 (+/-3)<br>2555 (+/-2)<br>4935 (+/-3)<br>4935 (+/-3)<br>4986 (+/-3)<br>5008 (+/-3)<br>5025 (+/-3)<br>6228 (+/-5)<br>6617 (+/-5) | 4265 (+/-2)<br>4938 (+/-2)<br>4989 (+/-3)<br>5027 (+/-2)<br>6230 (+/-3)<br>6387 (+/-4)<br>6619 (+/-3) | 1317 (+/-4)<br>1440 (+/-4)<br>3761 (+/-1)<br>4262 (+/-2)<br>4936 (+/-3)<br>4987 (+/-3)<br>5008 (+/-2)<br>6038 (+/-4)<br>6230 (+/-4)<br>6256 (+/-5)<br>6619 (+/-5) |

FIGURE 3-3

| *S.cohni urealyticum* | | | | *S.schleiferi coagulans* | | |
|---|---|---|---|---|---|---|
| 2075 (+/-1) | 1357 (+/-1) | 2077 (+/-2) | 1318 (+/-2) | 4276 (+/-4) | 1004 (+/-2) | 4853 (+/-3) | 2135 (+/-2) |
| 2098 (+/-1) | 2074 (+/-1) | 2115 (+/-2) | 1442 (+/-3) | 4851 (+/-4) | 4852 (+/-4) | 4875 (+/-3) | 2820 (+/-1) |
| 2114 (+/-1) | 2097 (+/-1) | 2406 (+/-3) | 2075 (+/-3) | 4873 (+/-4) | 4874 (+/-4) | 4891 (+/-3) | 3506 (+/-1) |
| 2136 (+/-2) | 2114 (+/-1) | 6080 (+/-2) | 2098 (+/-3) | 4889 (+/-4) | 4890 (+/-3) | 6774 (+/-4) | 4854 (+/-2) |
| 6079 (+/-3) | 2135 (+/-2) | 6118 (+/-2) | 2114 (+/-2) | 4984 (+/-4) | 4987 (+/-4) | | 4876 (+/-2) |
| 6541 (+/-4) | 2153 (+/-1) | 6542 (+/-2) | 4898 (+/-3) | 6683 (+/-6) | 6571 (+/-5) | | 4987 (+/-1) |
| | 2441 (+/-1) | 6580 (+/-2) | 6083 (+/-4) | 6771 (+/-6) | 6685 (+/-6) | | 6405 (+/-5) |
| | 4895 (+/-2) | | 6545 (+/-4) | | 6773 (+/-7) | | 6573 (+/-6) |
| | 6079 (+/-3) | | | | | | 6688 (+/-6) |
| | 6118 (+/-3) | | | | | | 6775 (+/-6) |
| | 6540 (+/-4) | | | | | | |
| | 6579 (+/-4) | | | | | | |

| *S.epidermidis* | | | | *S.schleiferi schleiferi* | | |
|---|---|---|---|---|---|---|
| 2836 (+/-4) | 2256 (+/-1) | 2738 (+/-2) | 2485 (+/-2) | 2577 (+/-2) | 2575 (+/-1) | 2577 (+/-2) | 2573 (+/-4) |
| 5340 (+/-2) | 4102 (+/-4) | 2882 (+/-3) | 2735 (+/-3) | 2670 (+/-2) | 2633 (+/-1) | 2672 (+/-2) | 2634 (+/-3) |
| 6682 (+/-4) | 4478 (+/-4) | 5341 (+/-2) | 2845 (+/-3) | 2692 (+/-2) | 2669 (+/-1) | 2924 (+/-2) | 2669 (+/-3) |
| 6720 (+/-4) | 4938 (+/-5) | 6684 (+/-2) | 5340 (+/-3) | 2708 (+/-2) | 2690 (+/-1) | 2946 (+/-2) | 2905 (+/-3) |
| | 4979 (+/-5) | | 6685 (+/-5) | 2922 (+/-2) | 2707 (+/-1) | 2962 (+/-2) | 2921 (+/-3) |
| | 4996 (+/-4) | | 6821 (+/-4) | 2944 (+/-2) | 2920 (+/-1) | | 2943 (+/-3) |
| | 5017 (+/-4) | | | 2961 (+/-2) | 2942 (+/-1) | | 2960 (+/-3) |
| | 5035 (+/-5) | | | 2983 (+/-2) | 2959 (+/-1) | | 2974 (+/-3) |
| | 5132 (+/-4) | | | 3000 (+/-2) | 2982 (+/-1) | | 3059 (+/-3) |
| | 6890 (+/-7) | | | | 2998 (+/-1) | | |

FIGURE 4-1

| Species | | | | | Species | | | | |
|---|---|---|---|---|---|---|---|---|---|
| S.haemolyticus | 4981 (+/-3)<br>4997 (+/-3)<br>5036 (+/-3)<br>5131 (+/-3)<br>6891 (+/-5) | 2256 (+/-1)<br>4102 (+/-4)<br>4478 (+/-4)<br>4938 (+/-5)<br>4979 (+/-5)<br>4996 (+/-4)<br>5017 (+/-4)<br>5035 (+/-5)<br>5132 (+/-4)<br>6890 (+/-7) | 4982 (+/-2)<br>4998 (+/-2)<br>5133 (+/-2)<br>6892 (+/-2) | 1319 (+/-3)<br>1724 (+/-3)<br>2256 (+/-1)<br>4480 (+/-3)<br>4983 (+/-3)<br>4999 (+/-4)<br>5135 (+/-3)<br>6895 (+/-5) | S.sciuri sciuri | 1342 (+/-1)<br>1360 (+/-2)<br>1395 (+/-1)<br>1407 (+/-1)<br>1421 (+/-1)<br>1436 (+/-4)<br>5520 (+/-2)<br>5652 (+/-2) | 1004 (+/-2)<br>1328 (+/-2)<br>1340 (+/-2)<br>1355 (+/-2)<br>1380 (+/-2)<br>1394 (+/-3)<br>1406 (+/-3)<br>1419 (+/-3)<br>1433 (+/-2)<br>5518 (+/-4)<br>5650 (+/-4) | 1144 (+/-4)<br>2192 (+/-3)<br>5652 (+/-2) | 1356 (+/-4)<br>5522 (+/-2)<br>5654 (+/-2)<br>6501 (+/-3) |
| S.hominis hominis | 1138 (+/-2)<br>2839 (+/-2)<br>4564 (+/-2)<br>4695 (+/-2)<br>5223 (+/-2)<br>5356 (+/-2)<br>6476 (+/-2)<br>6609 (+/-2) | 2430 (+/-2)<br>4291 (+/-1)<br>4565 (+/-2)<br>4603 (+/-1)<br>4697 (+/-1)<br>5224 (+/-1)<br>6462 (+/-2)<br>6478 (+/-2)<br>6516 (+/-2) | 4565 (+/-3)<br>4697 (+/-3)<br>5224 (+/-3)<br>6477 (+/-3) | 4565 (+/-3)<br>5225 (+/-3)<br>6464 (+/-4)<br>6480 (+/-4)<br>6617 (+/-4) | S.simulans | 2780 (+/-1)<br>2893 (+/-1)<br>2933 (+/-2)<br>3958 (+/-2)<br>3996 (+/-1)<br>4094 (+/-2)<br>4321 (+/-2)<br>5694 (+/-3) | 2779 (+/-2)<br>2893 (+/-2)<br>2932 (+/-2)<br>3957 (+/-2)<br>3979 (+/-2)<br>3995 (+/-2)<br>4094 (+/-2)<br>5693 (+/-4) | 2743 (+/-2)<br>2782 (+/-3)<br>2896 (+/-3)<br>2935 (+/-3)<br>3960 (+/-2) | 1315 (+/-0)<br>2738 (+/-0)<br>2760 (+/-0)<br>2778 (+/-0)<br>2891 (+/-1)<br>2931 (+/-0)<br>3957 (+/-1)<br>3995 (+/-0)<br>4094 (+/-0)<br>5695 (+/-0) |
| S.hominis novobiosepticus | 2496 (+/-2)<br>2839 (+/-2)<br>4696 (+/-3)<br>4916 (+/-3)<br>5224 (+/-3)<br>6478 (+/-4) | 2497 (+/-2)<br>2536 (+/-2)<br>2839 (+/-2)<br>2858 (+/-2)<br>2996 (+/-3)<br>4565 (+/-1)<br>4696 (+/-1)<br>4916 (+/-1)<br>5225 (+/-1)<br>6478 (+/-2) | 1094 (+/-3)<br>1117 (+/-3)<br>1132 (+/-4)<br>1144 (+/-3)<br>2407 (+/-2)<br>2820 (+/-2)<br>4916 (+/-2)<br>6477 (+/-3) | 1318 (+/-3)<br>2820 (+/-3)<br>4565 (+/-3)<br>4916 (+/-3)<br>5225 (+/-3)<br>6440 (+/-5)<br>6463 (+/-5)<br>6479 (+/-4) | S. warneri | 2177 (+/-2)<br>2336 (+/-1)<br>2375 (+/-2)<br>2585 (+/-2)<br>2824 (+/-2)<br>2936 (+/-2)<br>5457 (+/-2)<br>5906 (+/-3)<br>5945 (+/-3) | 2176 (+/-2)<br>2215 (+/-2)<br>2336 (+/-2)<br>2358 (+/-2)<br>2375 (+/-2)<br>2585 (+/-2)<br>2624 (+/-2)<br>2785 (+/-2)<br>2807 (+/-2)<br>2824 (+/-2) | 2177 (+/-2)<br>2337 (+/-2)<br>2376 (+/-2)<br>2586 (+/-2)<br>2786 (+/-2)<br>2808 (+/-1)<br>2824 (+/-1)<br>2897 (+/-2)<br>2936 (+/-1)<br>5908 (+/-3) | 2175 (+/-2)<br>2335 (+/-2)<br>2555 (+/-1)<br>2584 (+/-2)<br>2605 (+/-2)<br>2622 (+/-2)<br>2756 (+/-1)<br>2784 (+/-1)<br>2805 (+/-1)<br>2823 (+/-1) |

FIGURE 4-2

| Species | Col 1 | Col 2 | Col 3 | Col 4 | Col 5 | Col 6 | Col 7 | Col 8 |
|---|---|---|---|---|---|---|---|---|
| S.intermedius | 2092 (+/-2)<br>2117 (+/-1)<br>2133 (+/-1)<br>2154 (+/-1)<br>2170 (+/-2)<br>4278 (+/-3)<br>4796 (+/-3)<br>6244 (+/-4)<br>6732 (+/-4)<br>6770 (+/-5) | 6516 (+/-2)<br>6614 (+/-2) | 1358 (+/-3)<br>2092 (+/-2)<br>2117 (+/-2)<br>2133 (+/-2)<br>2154 (+/-2)<br>2777 (+/-2)<br>2816 (+/-2)<br>4278 (+/-1)<br>4796 (+/-2)<br>6244 (+/-3)<br>6733 (+/-3)<br>6771 (+/-3) | 1378 (+/-2)<br>2094 (+/-2)<br>2135 (+/-2)<br>4279 (+/-2)<br>4797 (+/-2)<br>6245 (+/-2)<br>6733 (+/-2) | 2133 (+/-2)<br>4278 (+/-2)<br>4796 (+/-3)<br>6245 (+/-5)<br>6734 (+/-5)<br>6873 (+/-5) | | | |
| M. lentus | 6289 (+/-3)<br>6330 (+/-4)<br>6425 (+/-3) | 4332 (+/-1)<br>5221 (+/-1)<br>6287 (+/-1)<br>6309 (+/-2)<br>6328 (+/-1)<br>6425 (+/-3)<br>10218 (+/-4) | | | | | | |
| S.xylosus | | | | | 2429 (+/-2)<br>4236 (+/-2)<br>6065 (+/-2)<br>6386 (+/-3)<br>6572 (+/-3) | 2897 (+/-2)<br>2936 (+/-2)<br>5906 (+/-3) | | 2896 (+/-1)<br>2918 (+/-2)<br>2934 (+/-1)<br>5909 (+/-0) |
| | | | | | | 2111 (+/-3)<br>2429 (+/-3)<br>2450 (+/-4)<br>2467 (+/-3)<br>4895 (+/-3)<br>4962 (+/-3)<br>6064 (+/-4)<br>6385 (+/-4)<br>6571 (+/-4) | 1119 (+/-2)<br>1145 (+/-4)<br>1364 (+/-3)<br>4238 (+/-2)<br>6066 (+/-2)<br>6387 (+/-2)<br>6525 (+/-2)<br>6573 (+/-2) | 1140 (+/-3)<br>3808 (+/-2)<br>4234 (+/-2)<br>4894 (+/-1)<br>6064 (+/-0)<br>6386 (+/-0)<br>6501 (+/-1)<br>6523 (+/-0)<br>6572 (+/-0) |
| M. luteus | | | | | 1347 (+/-4)<br>2794 (+/-2)<br>4332 (+/-2)<br>5251 (+/-3)<br>6247 (+/-2)<br>6286 (+/-3) | 1345 (+/-2)<br>2794 (+/-1)<br>4332 (+/-2)<br>5471 (+/-2)<br>5924 (+/-2)<br>6247 (+/-2)<br>6268 (+/-3)<br>6287 (+/-2)<br>6287 (+/-2)<br>6430 (+/-3)<br>7235 (+/-4)<br>7388 (+/-4)<br>9513 (+/-6) | 1007 (+/-3)<br>1145 (+/-3)<br>1167 (+/-3)<br>1183 (+/-3)<br>1343 (+/-2)<br>2192 (+/-3)<br>2795 (+/-3)<br>4333 (+/-3)<br>6248 (+/-2)<br>6432 (+/-3) | 1131 (+/-3)<br>1314 (+/-3)<br>1318 (+/-1)<br>1330 (+/-2)<br>1340 (+/-1)<br>1356 (+/-0)<br>2635 (+/-1)<br>2793 (+/-1)<br>4334 (+/-3)<br>5254 (+/-3)<br>5475 (+/-3)<br>6252 (+/-4)<br>6293 (+/-5) |

FIGURE 4-3

| CIP 7612ST | CIP 103545 | CIP 105261 | CIP 105262 | CIP 8157 | CIP 104689 | CIP 105719 | CIP 8160T | CIP 106511 | CIP 8165 | CIP 103540 | CIP 8162 | CIP 103583 | CIP 105825 |
|---|---|---|---|---|---|---|---|---|---|---|---|---|---|
| 1000 1005 | 1015 1321 | 1136 1134 | 1135 1046 | 2178 2172 | 2178 1005 | 1001 1089 | 2543 2441 | 5080 2113 | 1112 2255 | 2174 2172 | 1096 1004 | 1001 2072 | 1060 1134 |
| 1435 1012 | 1100 1480 | 1236 1147 | 1153 1073 | 2200 2195 | 2216 1080 | 1016 1102 | 2566 2606 | 5097 2430 | 1134 4474 | 2212 2211 | 1110 1019 | 1016 2094 | 1079 1323 |
| 1438 1020 | 1431 1604 | 1257 1150 | 2493 1089 | 2338 2332 | 2353 1103 | 1018 1116 | 2582 2638 | 5119 2452 | 1216 4606 | 2349 2347 | 1113 2640 | 1039 2111 | 1098 1340 |
| 2121 1028 | 1435 1606 | 1317 1171 | 2532 1112 | 2377 2371 | 2376 1105 | 1058 1139 | 2608 2660 | 5135 2469 | 1315 4976 | 2372 2389 | 1131 2560 | 2412 2133 | 1102 1356 |
| 2350 1043 | 1473 2127 | 1356 1185 | 2649 1153 | 2586 2392 | 2395 1117 | 1060 1158 | 2644 2676 | 5157 2508 | 1354 4995 | 2391 2428 | 1313 2678 | 2550 2149 | 1117 1379 |
| 2474 1082 | 2121 2479 | 1394 1216 | 2818 1324 | 2625 2409 | 2417 1119 | 1060 1178 | 2740 2698 | 5174 2619 | 1392 5013 | 2412 2780 | 1352 2715 | 2589 2417 | 1139 1393 |
| 2512 1100 | 2172 2497 | 2428 1232 | 2835 1437 | 2787 2430 | 2434 1119 | 1074 1181 | 2778 2714 | 5233 4237 | 1417 5030 | 2430 2802 | 1353 2918 | 2639 2418 | 1177 1417 |
| 2551 1142 | 2211 2518 | 2447 1255 | 2856 2087 | 2809 2581 | 2471 1140 | 1074 1314 | 2918 2904 | 6714 4896 | 1689 5125 | 2592 2819 | 1375 2954 | 2661 4477 | 1324 2473 |
| 2824 1443 | 2427 2541 | 2644 1269 | 2874 2089 | 2825 2620 | 2597 1143 | 1076 1329 | 3073 2926 | 6752 4963 | 2109 5498 | 2781 2840 | 1393 5211 | 2678 6071 | 1341 2632 |
| 4259 1481 | 2473 2556 | 2836 1315 | 4696 2113 | 2847 2657 | 2786 1143 | 1098 1343 | 4347 2943 | 6065 | 2263 6886 | 2804 2861 | 1412 7040 | 2698 6537 | 1357 2751 |
| 4932 1695 | 2496 2830 | 3677 1338 | 4915 2129 | 2937 2803 | 2808 1159 | 1113 1356 | 4385 5096 | 6103 | 2425 | 2820 2884 | 1434 | 2715 | 1361 2790 |
| 4970 1784 | 2512 4264 | 4560 1354 | 5224 2151 | 5458 2820 | 2825 1315 | 1113 1367 | 4457 5117 | 6386 | 2448 | 2843 2901 | 1484 | 2917 | 1381 4330 |
| 4983 2048 | 2536 4937 | 4598 1392 | 6479 2164 | 5907 2879 | 2847 1331 | 1114 1381 | 4495 5134 | 6524 | 2464 | 2863 2920 | 2128 | 2955 | 1395 5249 |
| 5006 2075 | 2550 4988 | 4691 1434 | 2587 | 5945 2893 | 2867 1343 | 1118 1395 | 4564 6712 | 6572 | 2502 | 2886 2938 | 2168 | 5214 | 1419 5471 |
| 5021 2086 | 2551 5025 | 4730 2277 | 2772 | 2932 | 2890 1358 | 1134 1421 | 4602 6733 | 6610 | 2615 | 2902 4525 | 2169 |  | 1438 5509 |
| 5063 2099 | 2804 5894 | 5219 2316 | 2810 | 2969 | 2906 1370 | 1136 1433 | 4950 6750 |  | 2785 | 2922 | 2264 |  | 2072 6247 |
| 6226 2114 | 2822 6038 | 5257 2836 | 3785 | 5456 | 2927 1384 | 1153 1445 | 5162 |  | 3322 | 2939 | 2302 |  | 2095 6269 |
| 6263 2127 | 2883 6289 | 5350 4564 | 4274 | 5905 | 2945 1385 | 1156 1462 | 5200 |  | 4234 | 4523 | 2527 |  | 2111 6286 |
| 6615 2355 | 2884 6384 | 6470 4595 | 4311 | 5944 | 4531 1397 | 1169 1724 | 7355 |  | 4876 |  | 2621 |  | 2130 6430 |
| 6653 2478 | 2900 6399 | 6492 4733 | 4793 |  | 1409 |  1170 2245 |  |  | 4893 |  | 2813 |  | 2399 6431 |
| 2499 | 2938 6618 | 6508 5222 | 4830 |  | 1424 | 1174 2709 |  |  | 4914 |  | 2841 |  | 2438 7390 |
| 2501 | 4260 | 6602 5261 | 5300 |  | 1435 | 1178 2718 |  |  | 4931 |  | 2853 |  | 4263 |
| 2517 | 4933 | 6640 5355 | 5844 |  | 1435 | 1192 2723 |  |  | 4960 |  | 2856 |  | 4895 |
| 2555 | 4985 | 6440 | 6242 |  | 1437 | 1195 2732 |  |  | 5028 |  | 4270 |  | 6081 |
| 2557 | 5023 | 6478 | 6342 |  | 1442 | 1232 2755 |  |  | 6065 |  | 4845 |  | 6101 |
| 2709 | 6287 | 6497 | 6717 |  | 1444 | 1309 2767 |  |  | 6103 |  | 4867 |  | 6118 |
| 2828 | 6381 | 6516 | 6731 |  | 1624 | 1314 2772 |  |  | 6200 |  | 4883 |  | 6139 |
| 2867 | 6398 | 6611 | 6750 |  | 2376 | 1325 2783 |  |  | 6386 |  | 4905 |  | 6157 |
| 4261 | 6616 | 6649 | 6769 |  | 2716 | 1338 2800 |  |  | 6525 |  | 4922 |  | 6217 |
| 4932 |  |  | 6785 |  | 2732 | 1362 2816 |  |  | 6571 |  | 4960 |  | 6388 |
| 4971 |  |  | 6791 |  | 2735 | 1363 2825 |  |  | 6610 |  | 4977 |  | 6544 |
| 4983 |  |  | 6807 |  | 2746 | 1377 2841 |  |  |  |  | 4999 |  | 6563 |
| 5004 |  |  | 6868 |  | 2755 | 1379 4305 |  |  |  |  | 5016 |  | 6581 |

FIGURE 4-4

| CIP 76125T | CIP 103545 | CIP 105261 | CIP 105262 | CIP 8157 | CIP 104689 | CIP 105719 | CIP 8160T | CIP 106511 | CIP 8165 | CIP 103540 | CIP 8162 | CIP 103583 | CIP 105825 |
|---|---|---|---|---|---|---|---|---|---|---|---|---|---|
| 5021 | | | 9633 | | 2770 | 1382 4915 | | | | | 6396 | | |
| 5062 | | | | | 2774 | 1392 5518 | | | | | 6678 | | |
| 6031 | | | | | 2779 | 1403 5556 | | | | | 6717 | | |
| 6223 | | | | | 2785 | 1423 5650 | | | | | 6753 | | |
| 6242 | | | | | 2791 | 1428 5689 | | | | | 6766 | | |
| 6261 | | | | | 2801 | 1430 | | | | | 6786 | | |
| 6378 | | | | | 5521 | 1438 | | | | | 6804 | | |
| 6394 | | | | | 5652 | 1619 | | | | | | | |
| 6611 | | | | | 6632 | 1640 | | | | | | | |
| 6633 | | | | | | 1692 | | | | | | | |
| 6649 | | | | | | 1693 | | | | | | | |
| 6667 | | | | | | 1733 | | | | | | | |
| 6747 | | | | | | 1758 | | | | | | | |
| 6784 | | | | | | 1822 | | | | | | | |
| | | | | | | 1952 | | | | | | | |
| | | | | | | 1956 | | | | | | | |
| | | | | | | 2037 | | | | | | | |
| | | | | | | 2180 | | | | | | | |
| | | | | | | 2240 | | | | | | | |
| | | | | | | 2254 | | | | | | | |
| | | | | | | 2257 | | | | | | | |
| | | | | | | 2266 | | | | | | | |
| | | | | | | 2267 | | | | | | | |
| | | | | | | 2281 | | | | | | | |
| | | | | | | 2373 | | | | | | | |
| | | | | | | 2668 | | | | | | | |
| | | | | | | 4304 | | | | | | | |
| | | | | | | 4918 | | | | | | | |
| | | | | | | 5520 | | | | | | | |
| | | | | | | 5652 | | | | | | | |
| | | | | | | 5691 | | | | | | | |
| | | | | | | 6500 | | | | | | | |
| | | | | | | 6631 | | | | | | | |

FIGURE 5-1

*S.epidermidis*

```
LL1   LL2   LL3   LL4   LL5   LL6   LL7   LL8   LL9   LL10  LL11  LL12  LL13  LL14  LL15  LL16
1911  1041  2036  3344  2843  2420  5121  2841  3343  1234  3349  3344  2242  2246  3342  2841
2057  1234  2653  4298  2855  2458  5262  3345  5119  3344  3349  4298  2838  2840  5117  2854
2841  1577  2803  4678  3346  2842  5346  4299  5256  4298  4292  5119  3342  3343  5254  3343
3338  2419  2841  5120  4678  2855  6688  5120  5346  5120  5122  5257  3748  3746  5343  5119
5115  2458  2855  5251  5122  3345  6725  5261  6688  5262  5264  5346  5345  5119  6455  5260
5256  2842  3346  5345  5264  5122  6827  5347  6725  5345  5346  5394  5532  5261  6686  5345
5341  2853  3749  6688  5346  5264        6688  6826  6689  6688  6459  6689  5345  6723  6671
5888  2879  4679  6725  5397  5345        6726        6725  6726  6688  6725  6457  6822  6688
6582  3344  5122  6825  6462  5396        6827        6825  6824  6725  6934  6688        6725
6684  4299  5263        6688  6591                                      6825        6726        6824
6722  4678  5345        6725  6688
6820  5262  5396        6828  6726
8237  5346  6462              6828
8702  5395  6688
      6588  6828
      6690
      6724
      6825
```

```
CC4   ALA4  abm1  abm2  abm3  abm4  AMT1  AMT2  AMT3  AMT4  AMT5  AMT6  AMT7
2623  2494  1310  1151  2887  1151  1487  1486  1041  1486  1041  1797  2214
2663  2652  1442  2840  3339  2837  1517  1516  1488  1516  1458  2214  2419
4301  2671  1683  3341  3743  2881  2203  2213  1518  2201  1487  2419  2436
5122  2691  2191  4296  4900  3338  2418  2417  2215  2212  1501  2436  2457
5255  2841  2297  4901  5117  4293  2457  2437  2252  2417  1518  2457  2493
5344  2856  2630  5054  5344  4898  2554  2456  2420  2435  1531  2493  2854
6462  3344  2839  5345  6672  5342  2593  2841  2438  2457  1560  2840  2870
6688  5121  3332  6688  6686  6686  2752  2853  2458  2841  2173  2870  2889
6726  5253  4284  6725  6724  6724  2842  2876  2835  2853  2203  3345  4680
6829  5344  4888  6827  6825  6823  2854  4901  2889  2880  2215  4679  5345
            4926                    3344  5345  4680  3343  2233  4906  6689
      5344  4926              9634  3344  5345  4680  3343  2233  4906  6689
            6590                    4903  6688  4905  4903  2420  5345  6725
            6674  5295        9662  5119  6726  5345  5345  2436  6688
            6689  5332              5346  6826  6678  6688  2459  6725
            6725  5343              6688        6688  6826  2841
            6826  6388              6725              6688        2855
                  6659              6826              6726        2889
                  6685                                            2919
                  6815                                            3345
                  6832                                            4680
                  7542                                            4905
                                                                  5345
                                                                  6688
                                                                  6725
                                                                  6829
```

FIGURE 5-2

| mej1 | mej2 | dja | far1 | boc | faua1 | faua2 | rem | yos1 | yos2 | yos3 | sec2 | sec3 |
|------|------|------|------|------|-------|-------|------|------|------|------|------|------|
| 3341 | 3339 | 1636 | 2644 | 1523 | 1036 | 1457 | 1033 | 3341 | 2648 | 1036 | 3339 | 3339 |
| 4294 | 5116 | 3336 | 3335 | 1638 | 1159 | 1487 | 1427 | 4294 | 2850 | 1572 | 5116 | 5117 |
| 4899 | 5248 | 5113 | 4290 | 3341 | 1273 | 1517 | 1440 | 5340 | 5345 | 1688 | 5249 | 5249 |
| 5115 | 5343 | 5244 | 4670 | 5119 | 1273 | 2172 | 1468 | 6683 | 6689 | 2648 | 5343 | 5344 |
| 5341 | 6672 | 5339 | 5113 | 5251 | 1442 | 2203 | 1555 | 6817 | 6826 | 2851 | 6508 | 6508 |
| 6684 | 6688 | 6683 | 5245 | 5345 | 1525 | 2214 | 1567 |      |      | 3341 | 6687 | 6672 |
| 6720 | 6725 | 6721 | 5339 | 5479 | 1527 | 2418 | 2640 |      |      | 4296 | 6725 | 6688 |
| 6823 | 6823 | 6817 | 6666 | 6674 | 1551 | 2457 | 2679 |      |      | 4674 | 6824 | 6726 |
|      |      | 9657 | 6683 | 6688 | 1555 | 2554 | 2830 |      |      | 5345 |      | 6824 |
|      |      |      | 6817 | 6725 | 1558 | 2593 | 2835 |      |      | 6689 |      |      |
|      |      |      |      | 6826 | 1565 | 2752 | 2836 |      |      | 6727 |      |      |
|      |      |      |      |      | 1569 | 2842 | 2875 |      |      | 6825 |      |      |
|      |      |      |      |      | 1681 | 2854 | 2880 |      |      |      |      |      |
|      |      |      |      |      | 2010 | 2888 | 3335 |      |      |      |      |      |
|      |      |      |      |      | 2413 | 3344 | 3736 |      |      |      |      |      |
|      |      |      |      |      | 2426 | 4903 | 3774 |      |      |      |      |      |
|      |      |      |      |      | 2430 | 5119 | 4286 |      |      |      |      |      |
|      |      |      |      |      | 2833 | 5345 | 4663 |      |      |      |      |      |
|      |      |      |      |      | 2842 | 6673 | 5108 |      |      |      |      |      |
|      |      |      |      |      | 2847 | 6687 | 5240 |      |      |      |      |      |
|      |      |      |      |      | 2876 | 6727 | 5338 |      |      |      |      |      |
|      |      |      |      |      | 2880 | 6826 | 5370 |      |      |      |      |      |
|      |      |      |      |      | 3339 |      | 6390 |      |      |      |      |      |
|      |      |      |      |      | 3339 |      | 6576 |      |      |      |      |      |
|      |      |      |      |      | 3743 |      | 6684 |      |      |      |      |      |
|      |      |      |      |      | 4292 |      | 6722 |      |      |      |      |      |
|      |      |      |      |      | 4679 |      | 6748 |      |      |      |      |      |
|      |      |      |      |      | 4899 |      | 6813 |      |      |      |      |      |
|      |      |      |      |      | 5000 |      | 9614 |      |      |      |      |      |
|      |      |      |      |      | 5116 |      | 9643 |      |      |      |      |      |
|      |      |      |      |      | 5343 |      |      |      |      |      |      |      |
|      |      |      |      |      | 6690 |      |      |      |      |      |      |      |
|      |      |      |      |      | 6827 |      |      |      |      |      |      |      |

| omz1 | omz4 | ban1 | bem1 | bem2 | bem3 | bem5 | mah1 | mah2 | mah3 | mah4 | mah5 |
|------|------|------|------|------|------|------|------|------|------|------|------|
| 3340 | 3340 | 2837 | 1441 | 2839 | 2838 | 1035 | 1448 | 2837 | 2842 | 3337 | 2643 |
| 3743 | 3744 | 2877 | 2483 | 2877 | 2883 | 1451 | 1563 | 3339 | 3338 | 4293 | 2835 |
| 4295 | 4295 | 3337 | 2836 | 3342 | 3340 | 2137 | 3338 | 4294 | 5116 | 5115 | 2845 |
| 5115 | 5118 | 5114 | 2878 | 5119 | 5053 | 2837 | 4294 | 5116 | 5252 | 5342 | 3337 |
| 5342 | 5344 | 5340 | 2883 | 5345 | 5344 | 2882 | 5116 | 5254 | 5342 | 6670 | 5115 |
| 6684 | 6673 | 6668 | 3332 | 6674 | 6687 | 3340 | 5248 | 5342 | 6671 | 6688 | 5250 |
| 6719 | 6688 | 6684 | 5336 | 6688 | 6725 | 3742 | 5342 | 6402 | 6687 | 6725 | 5342 |
| 6820 | 6725 | 6723 | 6120 | 6725 | 6825 | 4295 | 6671 | 6688 | 6725 | 6824 | 6688 |
|      | 6827 | 6820 | 6655 | 6826 |      | 5117 | 6686 | 6725 | 6824 |      | 6724 |
|      |      |      | 6684 |      |      | 5344 | 6724 | 6823 |      |      | 6824 |
|      |      |      | 6725 |      |      | 6586 | 6821 |      |      |      |      |
|      |      |      | 6809 |      |      | 6686 |      |      |      |      |      |
|      |      |      |      |      |      | 6725 |      |      |      |      |      |
|      |      |      |      |      |      | 6825 |      |      |      |      |      |
|      |      |      |      |      |      | 9635 |      |      |      |      |      |
|      |      |      |      |      |      | 9663 |      |      |      |      |      |

FIGURE 5-3

| mal1 | mal2 | mal3 | mal4 | dew2 | blf1 | blf2 | blf3 | guc1 | guc2 | taj1 | gau1 | gau2 | gau3 | gau4 | gau5 |
|---|---|---|---|---|---|---|---|---|---|---|---|---|---|---|---|
| 3338 | 2410 | 1036 | 2415 | 1039 | 1032 | 1037 | 3340 | 3343 | 1441 | 1033 | 1439 | 1131 | 1156 | 1449 | 1165 |
| 4293 | 3337 | 3339 | 3340 | 3340 | 2134 | 1452 | 4900 | 5117 | 1556 | 1226 | 1516 | 1146 | 1271 | 1563 | 1280 |
| 4897 | 4898 | 4900 | 4900 | 4899 | 3337 | 2138 | 5118 | 5249 | 2647 | 1524 | 1631 | 1163 | 1325 | 3341 | 1334 |
| 5114 | 5115 | 5117 | 5117 | 5115 | 3740 | 3341 | 5344 | 5343 | 2836 | 1553 | 5345 | 1264 | 1439 | 5117 | 1449 |
| 5340 | 5341 | 5344 | 5344 | 5342 | 4898 | 4901 | 6589 | 6584 | 2850 | 2836 | 6685 | 1278 | 1554 | 5342 | 1563 |
| 6665 | 6670 | 6688 | 6673 | 6685 | 5115 | 5118 | 6673 | 6669 | 3337 | 3337 |  | 1333 | 1567 | 6686 | 1732 |
| 6682 | 6686 | 6726 | 6689 | 6723 | 5341 | 5344 | 6689 | 6685 | 3742 | 3740 |  | 1416 | 1681 | 6822 | 1847 |
| 6818 | 6823 | 6824 | 6725 | 6820 | 6585 | 6689 | 6725 | 6820 | 5116 | 5115 |  | 1428 | 1723 |  | 3341 |
| 8232 | 8242 | 8243 | 6825 |  | 6686 | 6826 | 6825 |  | 5248 | 5341 |  | 1431 | 1837 |  | 5343 |
| 8697 | 8708 | 8709 |  |  | 6723 |  |  |  | 5343 | 6585 |  | 1447 | 2840 |  | 6671 |
|  |  |  |  |  | 6823 |  |  |  | 6588 | 6686 |  | 1547 | 3333 |  | 6686 |
|  |  |  |  |  |  |  |  |  | 6673 | 6724 |  | 1561 | 5109 |  | 6725 |
|  |  |  |  |  |  |  |  |  | 6688 | 6825 |  | 1730 | 5335 |  | 6822 |
|  |  |  |  |  |  |  |  |  | 6823 |  |  | 1830 | 6663 |  |  |
|  |  |  |  |  |  |  |  |  |  |  |  | 1845 | 6680 |  |  |
|  |  |  |  |  |  |  |  |  |  |  |  | 2014 | 6717 |  |  |
|  |  |  |  |  |  |  |  |  |  |  |  | 2130 | 6816 |  |  |
|  |  |  |  |  |  |  |  |  |  |  |  | 3339 |  |  |  |
|  |  |  |  |  |  |  |  |  |  |  |  | 5116 |  |  |  |
|  |  |  |  |  |  |  |  |  |  |  |  | 5342 |  |  |  |
|  |  |  |  |  |  |  |  |  |  |  |  | 6670 |  |  |  |
|  |  |  |  |  |  |  |  |  |  |  |  | 6687 |  |  |  |
|  |  |  |  |  |  |  |  |  |  |  |  | 6725 |  |  |  |
|  |  |  |  |  |  |  |  |  |  |  |  | 6821 |  |  |  |

| faa1 | ves2 | ves4 | ves5 | ves6 | fes2 | fes3 | lem1 | lem2 | lea1 | lea2 |
|---|---|---|---|---|---|---|---|---|---|---|
| 3339 | 3336 | 2490 | 1035 | 3339 | 2414 | 1166 | 3337 | 2834 | 2485 | 2646 |
| 4293 | 5114 | 2648 | 2490 | 4294 | 3339 | 1449 | 4293 | 3337 | 2549 | 2685 |
| 5116 | 5341 | 2797 | 2648 | 5116 | 4899 | 1563 | 5116 | 3741 | 2645 | 2848 |
| 5250 | 6585 | 2839 | 2798 | 5343 | 5116 | 1734 | 5342 | 4293 | 2847 | 3340 |
| 5312 | 6669 | 2849 | 2838 | 6671 | 5342 | 3343 | 6688 | 5116 | 3338 | 3743 |
| 5342 | 6686 | 2888 | 2849 | 6687 | 5342 | 4900 | 6724 | 5342 | 4294 | 4671 |
| 6401 | 6823 | 3342 | 2871 | 6824 | 6688 | 5117 | 6825 | 6688 | 4672 | 5118 |
| 6671 | 9664 | 3745 | 2889 |  | 6725 | 5343 |  | 6825 | 5117 | 5251 |
| 6686 |  | 4297 | 3340 |  | 6824 | 6688 |  |  | 5249 | 5345 |
| 6724 |  | 4674 | 3744 |  | 8708 | 6824 |  |  | 5343 | 6460 |
| 6827 |  | 5120 | 4296 |  |  | 8708 |  |  | 6585 | 6674 |
| 6844 |  | 5345 | 4674 |  |  |  |  |  | 6672 | 6688 |
| 7556 |  | 6691 | 5118 |  |  |  |  |  | 6689 | 6726 |
| 9216 |  | 6726 | 5309 |  |  |  |  |  | 6824 | 6827 |
|  |  | 6830 | 5345 |  |  |  |  |  | 9638 | 8101 |
|  |  | 9667 | 6588 |  |  |  |  |  | 9666 | 9639 |
|  |  |  | 6673 |  |  |  |  |  |  | 9665 |
|  |  |  | 6689 |  |  |  |  |  |  |  |
|  |  |  | 6727 |  |  |  |  |  |  |  |
|  |  |  | 6826 |  |  |  |  |  |  |  |
|  |  |  | 9638 |  |  |  |  |  |  |  |
|  |  |  | 9666 |  |  |  |  |  |  |  |

FIGURE 5-4

*S.warneri*

| CC1 | CC2 | CC3 | del | kho1 | kho2 |
|---|---|---|---|---|---|
| 2185 | 2185 | 2184 | 1387 | 2380 | 1406 |
| 2224 | 2345 | 2223 | 2177 | 2585 | 1440 |
| 2338 | 2384 | 2344 | 2309 | 2786 | 1554 |
| 2356 | 2594 | 2367 | 2337 | 2897 | 1699 |
| 2474 | 2777 | 2383 | 2557 | 2947 | 1786 |
| 2512 | 2795 | 2593 | 2586 | 4970 | 1857 |
| 2594 | 2817 | 2776 | 2625 | 5457 | 1988 |
| 2633 | 2833 | 2794 | 2758 | 5906 | 2011 |
| 2795 | 2907 | 2816 | 2786 | 6042 | 2337 |
| 2833 | 2932 | 2832 | 2824 | | 2356 |
| 2936 | 5466 | 2906 | 2869 | | 2382 |
| 5915 | 5915 | 2930 | 2897 | | 2586 |
| | | 2945 | 5906 | | 2786 |
| | | 5914 | | | 2825 |
| | | | | | 2835 |
| | | | | | 2898 |
| | | | | | 3002 |
| | | | | | 3337 |
| | | | | | 3739 |
| | | | | | 3823 |
| | | | | | 4829 |
| | | | | | 4972 |
| | | | | | 5083 |
| | | | | | 5115 |
| | | | | | 5248 |
| | | | | | 5352 |
| | | | | | 5390 |
| | | | | | 5459 |
| | | | | | 5478 |
| | | | | | 5894 |
| | | | | | 5910 |
| | | | | | 6045 |
| | | | | | 6242 |
| | | | | | 6457 |

FIGURE 5-5

*S.haemolyticus*

| ALA1 | ban2 | ban3 | ban4 | ban5 | ban6 | rib2 | rib3 | rib4 | rib5 | fes1 | marn1 | marn2 |
|------|------|------|------|------|------|------|------|------|------|------|-------|-------|
| 1668 | 2236 | 1016 | 1267 | 1321 | 2236 | 2492 | 535  | 2255 | 2491 | 1131 | 4477  | 1444  |
| 1725 | 3443 | 1030 | 1695 | 2259 | 3445 | 3441 | 657  | 2490 | 4292 | 1267 | 4996  | 4477  |
| 2256 | 4481 | 1045 | 1949 | 2496 | 3922 | 4478 | 738  | 4982 | 4480 | 1334 | 5038  | 4938  |
| 2273 | 4613 | 1071 | 4481 | 3445 | 4296 | 4610 | 762  | 4998 | 4612 | 1363 | 5130  | 4995  |
| 2296 | 4999 | 1109 | 4613 | 3922 | 4467 | 4940 | 780  | 5131 | 4941 | 2254 | 6892  | 5016  |
| 2494 | 5134 | 1126 | 4999 | 4295 | 4484 | 4981 | 794  | 6895 | 4998 | 2259 |       | 5036  |
| 4481 | 6471 | 1137 | 5134 | 4483 | 4616 | 4999 | 838  |      | 5131 | 2295 |       | 5129  |
| 4583 | 6877 | 1157 | 6471 | 4617 | 4986 | 5039 | 854  |      | 6894 | 2737 |       | 6891  |
| 4593 | 6894 | 1271 | 6687 | 4677 | 5000 | 5131 | 862  |      |      | 4293 |       |       |
| 4758 | 7030 | 1326 | 6878 | 5001 | 5136 | 5150 | 968  |      |      | 4478 |       |       |
| 4943 |      | 1341 | 6894 | 5135 | 6474 | 6497 | 4989 |      |      | 4611 |       |       |
| 5000 |      | 1394 | 7031 | 5864 | 6882 | 6894 | 5004 |      |      | 4997 |       |       |
| 5042 |      | 1443 | 9003 | 5940 | 6895 |      | 5138 |      |      | 5040 |       |       |
| 6895 |      | 1478 |      | 6379 | 7034 |      | 6901 |      |      | 5136 |       |       |
|      |      | 1508 |      | 6473 | 9009 |      |      |      |      | 6470 |       |       |
|      |      | 1556 |      | 6787 |      |      |      |      |      | 6893 |       |       |
|      |      | 1580 |      | 6881 |      |      |      |      |      | 9000 |       |       |
|      |      | 1693 |      | 6895 |      |      |      |      |      |      |       |       |
|      |      | 1708 |      | 7034 |      |      |      |      |      |      |       |       |
|      |      | 1724 |      | 9007 |      |      |      |      |      |      |       |       |
|      |      | 1840 |      | 9710 |      |      |      |      |      |      |       |       |
|      |      | 1897 |      |      |      |      |      |      |      |      |       |       |
|      |      | 1932 |      |      |      |      |      |      |      |      |       |       |
|      |      | 1946 |      |      |      |      |      |      |      |      |       |       |
|      |      | 2012 |      |      |      |      |      |      |      |      |       |       |
|      |      | 2033 |      |      |      |      |      |      |      |      |       |       |
|      |      | 2126 |      |      |      |      |      |      |      |      |       |       |
|      |      | 2223 |      |      |      |      |      |      |      |      |       |       |
|      |      | 2232 |      |      |      |      |      |      |      |      |       |       |
|      |      | 2257 |      |      |      |      |      |      |      |      |       |       |
|      |      | 2274 |      |      |      |      |      |      |      |      |       |       |
|      |      | 2295 |      |      |      |      |      |      |      |      |       |       |
|      |      | 2313 |      |      |      |      |      |      |      |      |       |       |
|      |      | 3130 |      |      |      |      |      |      |      |      |       |       |
|      |      | 3918 |      |      |      |      |      |      |      |      |       |       |
|      |      | 4292 |      |      |      |      |      |      |      |      |       |       |
|      |      | 4479 |      |      |      |      |      |      |      |      |       |       |
|      |      | 4515 |      |      |      |      |      |      |      |      |       |       |
|      |      | 4612 |      |      |      |      |      |      |      |      |       |       |
|      |      | 4672 |      |      |      |      |      |      |      |      |       |       |
|      |      | 4998 |      |      |      |      |      |      |      |      |       |       |
|      |      | 5136 |      |      |      |      |      |      |      |      |       |       |
|      |      | 6469 |      |      |      |      |      |      |      |      |       |       |
|      |      | 6895 |      |      |      |      |      |      |      |      |       |       |
|      |      | 7030 |      |      |      |      |      |      |      |      |       |       |

FIGURE 5-6

*S.hominis hominis*

| AVL1 | AVL2 | dew1 | ves1 |
|------|------|------|------|
| 1324 | 1718 | 1121 | 1278 |
| 1716 | 1834 | 1448 | 1447 |
| 1832 | 1978 | 3235 | 1561 |
| 2416 | 2435 | 3339 | 1716 |
| 2434 | 2454 | 3741 | 1731 |
| 2453 | 2470 | 4565 | 1751 |
| 2470 | 2653 | 4696 | 1831 |
| 2615 | 2749 | 4897 | 1844 |
| 2635 | 2844 | 5223 | 2433 |
| 2653 | 2874 | 5339 | 3235 |
| 2747 | 3002 | 6474 | 4566 |
| 2750 | 3027 | 6610 | 4699 |
| 2842 | 3044 | 6680 | 6462 |
| 2874 | 3239 | 6816 | 6478 |
| 3001 | 4570 |      | 6614 |
| 3026 | 5228 |      |      |
| 3043 | 6480 |      |      |
| 3238 | 6617 |      |      |
| 4567 |      |      |      |
| 5226 |      |      |      |
| 6479 |      |      |      |

*S.hominis novobiosepticus*

| ALA2 | ALA3 | mbt  | rib1 | taj2 | ves3 |
|------|------|------|------|------|------|
| 1086 | 1721 | 1156 | 1317 | 1160 | 1276 |
| 1101 | 1836 | 1256 | 1711 | 1317 | 1445 |
| 1117 | 1866 | 1269 | 1826 | 1440 | 1559 |
| 2431 | 1981 | 1317 | 1970 | 3234 | 1729 |
| 2494 | 2439 | 1324 | 2429 | 4564 | 1843 |
| 2532 | 2497 | 1423 | 2838 | 4696 | 2494 |
| 2656 | 2539 | 1439 | 3022 | 4917 | 3234 |
| 3000 | 2654 | 1554 | 3233 | 5225 | 4565 |
| 5228 | 2754 | 1610 | 4565 | 6480 | 6476 |
| 6475 | 2839 | 1709 | 4697 | 6518 |      |
| 6789 | 2856 | 1723 | 5226 | 6617 |      |
| 7143 | 4576 | 1824 | 6480 |      |      |
| 7402 | 5226 | 1838 |      |      |      |
| 9330 | 6481 | 1969 |      |      |      |
|      | 6628 | 2007 |      |      |      |
|      |      | 2121 |      |      |      |
|      |      | 2274 |      |      |      |
|      |      | 2426 |      |      |      |
|      |      | 4543 |      |      |      |
|      |      | 4560 |      |      |      |
|      |      | 4693 |      |      |      |
|      |      | 4911 |      |      |      |
|      |      | 5220 |      |      |      |
|      |      | 6475 |      |      |      |

FIGURE 5-7

*S.saprophyticus bovis*

| fel |
|---|
| 1441 |
| 2788 |
| 2826 |
| 3299 |
| 3757 |
| 3942 |
| 4930 |
| 4982 |
| 6032 |
| 6378 |
| 6566 |
| 6594 |
| 6612 |
| 6747 |
| 7874 |
| 7890 |
| 8026 |

*S.saprophyticus saprophyticus*

| | | | | |
|---|---|---|---|---|
| 1272 | 2829 | 3301 | 1020 | 2826 |
| 1319 | 3756 | 3756 | 1030 | 3107 |
| 1325 | 4258 | 4259 | 1034 | 3301 |
| 1440 | 4930 | 4930 | 1036 | 3757 |
| 1446 | 4982 | 4983 | 1040 | 4931 |
| 1556 | 5063 | 5065 | 1045 | 4983 |
| 1726 | 6563 | 6030 | 1052 | 6206 |
| 1904 | 6611 | 6175 | 1060 | 6222 |
| 2253 | 7887 | 6376 | 1062 | 6358 |
| 2793 | | 6537 | 1082 | 6375 |
| 2827 | | 6617 | 1443 | 6612 |
| 3302 | | | 2127 | |
| 3385 | | | 2480 | |
| 3757 | | | 2830 | |
| 3943 | | | 3762 | |
| 4933 | | | 4265 | |
| 4985 | | | 4938 | |
| 5069 | | | 4975 | |
| 6033 | | | 4990 | |
| 6376 | | | 5028 | |
| 6566 | | | 6231 | |
| 6613 | | | 6387 | |
| 7874 | | | 6621 | |
| 7890 | | | | |
| 8025 | | | | |

FIGURE 6-1

Aerobic or facultative aeroanaerobic Bacteria

A- Aerobic or facultative aeroanaerobic bacteria

A-1 Gram positive cocci

A-1-1 Catalase positive

*Staphylococcus, Micrococcus*

A-1-2 Catalase negative

*Streptococcus* (including *S. pneumoniae*), *Enterococcus, Aerococcus, Pediococcus, Gemella, Lactococcus, Leuconostoc*

A-2 Gram positive bacilli

*Corynebacterium, Listeria, Bacillus, Nocardia, Rhodococcus, Erysipelothrix,* some *Actinomyces, Lactobacillus*

A-3 Gram negative cocci

*Neisseria, Moraxella catarrhalis*

A-4 Oxydase negative Gram negative bacilli which grow on usual medium

*Enterobactéria, Acinetobacter, Pseudomonas oryzihabitans et P. luteola, Stenotrophomonas* (slow oxydase)

A-5 Oxydase positive Gram negative bacilli which grow on usual medium

*Pseudomonas* except *P. oryzihabitans* and *P. luteola, Burkholderia, Ralstonia, Brevundimonas, Alcaligenes, Achromobacter, Schewanella, Aeromonas, Plesiomonas, Flavobacterium, Sphingomonas, Comamonas, Chryseobacterium, Sphingobacterium, Ochrobactrum, Rhizobium, Inquilinus limosus, Bordetella* except *B. pertussis, Pasteurella, Vibrio, Moraxella osloensis*

FIGURE 6-2

A-6 Gram negative bacilli which grow on blood or chocolate agar

*Haemophilus, Actinobacillus, Cardiobacterium, Eikenella, Kingella, Brucella, Capnocytophaga, Francisella, Moraxella lacunata*

B - Strict anaerobic bacteria

B-1 Gram positive cocci

*Peptococcus, Peptostreptococcus*

B-2 Gram positive bacilli

*Clostridium, Eubacterium, Propionibacterium,* some *actinomyces, Bifidobacterium*

B-3 Gram negative bacilli

*Fusobacterium, Bacteroides, Porphyromonas, Prevotella*

B-4 Gram negative cocci

*Veillonella*

C - Bacteria requiring specific media and therefore a directed research

*Mycobacteria, Campylobacter, Helicobacter, Bordetella pertussis, Legionella, Borrelia/Spirochetes*

MEANS FOR IDENTIFYING A STRAIN ISOLATED FROM A CLINICAL SAMPLE AT THE SPECIES AND/OR SUBSPECIES LEVEL

This application is a Continuation-In-Part of International Application No. PCT/IB2008/001058, filed 8 Jan. 2008, which designated the U.S. and claims priority of EP Application No. 07290019.4, filed 8 Jan. 2007, the entire contents of each of which are all hereby incorporated herein by reference.

The invention relates to means for identifying a strain isolated from a clinical sample. It more particularly relates to a method for a precise and rapid identification at the species level and/or at the sub-species level of a clinical isolate by using Matrix assisted Laser Desorption Ionisation Time-Of-Flight Mass Spectrometry (MALDI-TOF-MS). It also relates to the databases used for this identification.

MALDI-TOF-MS is a technique used to examine the profile of proteins detected directly from intact bacterial cell surface.

This is a soft ionization method based on relative molecular masses allowing desorption of peptides and proteins from whole different cultured microorganisms. Ions are separated and detected according to their molecular mass and charge. The species are identified by their mass:charge ratio (m/z). This approach yields reproducible spectrum within minutes, consisting of series of peaks from 500 to 20000 m/z. Each peak corresponds to a molecular fragment released from the cell surface during laser desorption.

MALDI-TOF-MS has already been used for characterization of bacteria. However, among the various components identified in a spectra, only a few are present in a large population of germs of a given genospecies, the other are either isolate specific or vary upon growth conditions (media, temperature of incubation, . . . ) and cannot be used to identify the species or sub-species of a bacteria, and more generally of a germ.

The lack of a global strategy to identify within the spectra those peaks that can discriminate between various genospecies has hampered the use of MALDI-TOF-MS in routine clinical microbiology laboratories for the diagnostic of genospecies. Indeed these peaks have to correspond to components that are present in the majority of the isolates of a given genospecies and that are present in large quantity in the cell wall. Considering the possible variability inside a genospecies, it is likely that the characteristic of a genospecies does not rely on the presence of a single peak but rather on the presence of a set of peaks that are more or less conserved among the genospecies.

The inventors have found that such problems could be overcome (i) by performing a phenotypic analysis of the germ to be identified prior to the MALDI-TOF-MS analysis, and (ii) by carrying out the MALDI-TOF-MS analysis under specific conditions particularly concerning the choice of the matrix solution and reference data bases.

It is then an object of the invention to provide a new method based on MALDI-TOF-MS analysis for identifying a strain isolated from a clinical sample at the species and/or sub-species level.

It is another object of the invention to provide databases established from a set of strains with respect to a given germ.

The invention thus relates to a method for identifying at a species and/or sub-species level a strain isolated from a clinical sample using MALDI-TOF-MS analysis comprising eventually a step of classifying the strain in a group before performing the MALDI-TOF-MS analysis, wherein said analysis comprises the step of retaining in the spectrum of the tested strain the peaks having, compared to the peak with the highest intensity arbitrary set up to 1, a relative intensity which may vary depending on the germ, said relative intensity being then higher than 0.01 for germs such as fungi, and for most of the other germs higher than 0.02, particularly higher than 0.05, more particularly higher than 0.1.

The invention particularly relates to a method wherein said MALDI-TOF-MS analysis comprises the step of comparing the spectrum profile of the strain to be identified with a so-called reference database containing the characteristic MALDI-TOF-MS spectra of strains representative of the genospecies of the group of germs to which belongs said strain to be identified, said database containing for each representative strain, peaks having, compared to the peak with the highest intensity arbitrary set up to 1, a relative intensity which may vary depending on the germ, said relative intensity being then higher than 0.01 for germs such as fungi, and for most of the other germs higher than 0.02, particularly higher than 0.05, more particularly higher than 0.1, as far as they are present in at least 2 sub-cultures, preferably 5 or even 10 or more.

The selection of peaks as carried out according to the invention enables an accurate identification of the germ present in a clinical sample.

The classification step is based on the growth conditions and/or the characteristic of colonies and/or morphology of the bacteria upon microscopic examination and/or the gram stain and/or simple phenotypic tests.

The MALDI-TOF-MS technique is carried out on whole intact cells or on protein extracts obtained after lysis or corresponding to a fraction of the cellular components (cell wall, cytoplasm . . . ). This technique is ideally performed on an isolated colony of the strain to be identified, obtained from a clinical sample cultured on an appropriate growth medium and incubated at an appropriate temperature.

A matrix medium is added to the isolated colonies before performing the MALDI-TOF-MS technique.

For example, suitable matrix media comprise benzoic acid derivatives, such as hydroxyl benzoic acid, particularly 2,5-dihydroxybenzoic acid (DHB).

Other components may be present. For example, the matrix media may further comprise sinnapic acid. Such media are particularly appropriate for the identification of *Mycobacterium*.

Each spectrum is the sum of at least 300 laser shots, preferably more than 1 000, and even more than 2 000, from different regions of the well containing the strain to be analyzed, said spectrum being analyzed in a range of m/z from 500 to 50 000, and more preferably from 500 to 20 000, and more preferably from 2000 to 20000.

The profiles are then compared using a software which chooses the best match between the tested strain and the selected peaks of said reference database obtained by analyzing one or several reference strains specific of a given genospecies or genosubspecies. Each strain being a representative of one genospecies or genosubspecies of the group under study, so that the set of strains corresponds to the relevant genospecies or genosubspecies of one group of germs. The spectrum of each reference strain is recorded using the MALDI-TOF-MS technique. As above mentioned, the peak with the highest intensity is arbitrarily set up to 1, and all the other peaks have a value corresponding to the relative intensity of this highest peak. The peaks with a relative intensity being higher than 0.01 for germs such as fungi, and for most of the other germs higher than 0.02, or more particularly above 0.05 or more particularly above 0.1 present are retained, as far as they are present in at least 2 sub-cultures, preferably 5 or even 10 or more. These peaks are the selected peaks.

Considering some possible variation, the software chooses the best match between the tested strain and the database, taking into account a possible error of the m/z value. The range of the error is arbitrary set up to +/−20 or more preferably to +/−10.

The presence and absence of peaks are considered as fingerprints for a particular isolate.

Said method is a powerful tool for the fast identification of a germ, allowing to use it in the routine diagnosis of the laboratory. The requirement of expensive equipment is compensated by the very simple protocol, which requires minimum hands-on time. It is particularly appropriate for reference laboratories or hospitals receiving a high volume of samples.

The high resolution of the MALDI-TOF-MS method as performed according to the invention makes it possible for example to obtain characteristic spectral fingerprints for each species and even sub-species of a given germ.

Advantageously, said method is used for identifying germs selected in the group comprising bacteria, yeasts, fungi, molds such as filamentous fungi, particularly *Aspergilli* at the species and/or sub-species level.

According to a specific embodiment, the invention relates to the identification of species and/or sub-species of coagulase-negative *Staphylococci* (CNS in short).

The identification of CNS at the species level is not routinely performed as they are frequently considered as sample contaminations. In addition, the results of phenotypical methods performed on clinically significant strains are disappointing. Commercial identification kits are of limited value in identifying CNS isolates.

SodA sequence determination, despite to be the more accurate method for correct species identification of CNS, is time consuming, expensive, and technically demanding. In addition, although genotypic methods are clearly superior to phenotypic identifications, a drawback of sequence based genotypic methods may be a lack of quality of deposited sequences in data banks.

Thanks to the invention, the differentiation at the subspecies level is more accurate, for example for the subspecies of *Staphylococci*, with MALDI-TOF-MS than with SodA method, as it was shown that SodA gene does not well differentiate between the subspecies *S. capitis, S. hominis, S. saprophyticus* and *S. schleiferi*.

According to another embodiment, the invention relates to the identification of species or subspecies of non fermenting Gram negative *bacilli*, and other bacterial species of clinical relevance: *Streptococci*, gram positive *bacilli* (such as *Nocardia, corynebacteria* . . . ), enterobactericeae (such as *Escherichia coli, Klebsiella*, . . . ), mycobacteriaceae . . . .

In still another embodiment, the invention relates to the identification of yeast species particularly *Candida* or *Saccharomyces* species or subspecies such as illustrated by the Examples.

In a further embodiment, the invention provides means to identify at the species or subspecies level molds such as filamentous fungi of the *Aspergillus* species.

The databases used in the above defined identification method are also part of the invention.

They consist of a set of selected peaks obtained by MALDI-TOF-MS analysis of strains at least partially conserved among strains belonging to the same genospecies.

Preferably, said reference peaks correspond to major, conserved peaks with m/z above 0.01 for fungi, and above 0.02, more particularly above 0.05, more particularly above 0.1 with other germs.

Such databases are advantageously obtained for each group of germs by using a set of strains, each strain being the representative of one genospecies of the group under study, so that the set of strains corresponds to the relevant genospecies of one group of germs. The spectrum of each strain of such group is recorded using the MALDI-TOF-MS technique. Each strain is the representative of a genospecies of this group of germs, and is further designated as reference strain. As above mentioned, the peak with the highest intensity is arbitrarily set up to 1, all the other peaks have a value corresponding to the relative intensity of this highest peak. The major peaks are retained, such peaks preferably having a relative intensity of at least 0.01 with fungi and for most of the other germs at least 0.02, more particularly above 0.05, more particularly above 0.1. The peaks with a relative intensity above either 0.01 or 0.02, more particularly above 0.05 or more particularly above 0.1, depending of the germs present in all sets of data obtained for a given reference strain are then retained, as far as they are present in at least 2 sub-cultures, preferably 5 or even 10 or more.

The set of peaks thus obtained is specific of a genospecies for a given growth condition (medium and duration), and with respect to the characteristics of a given spectrometer.

Figure 2:
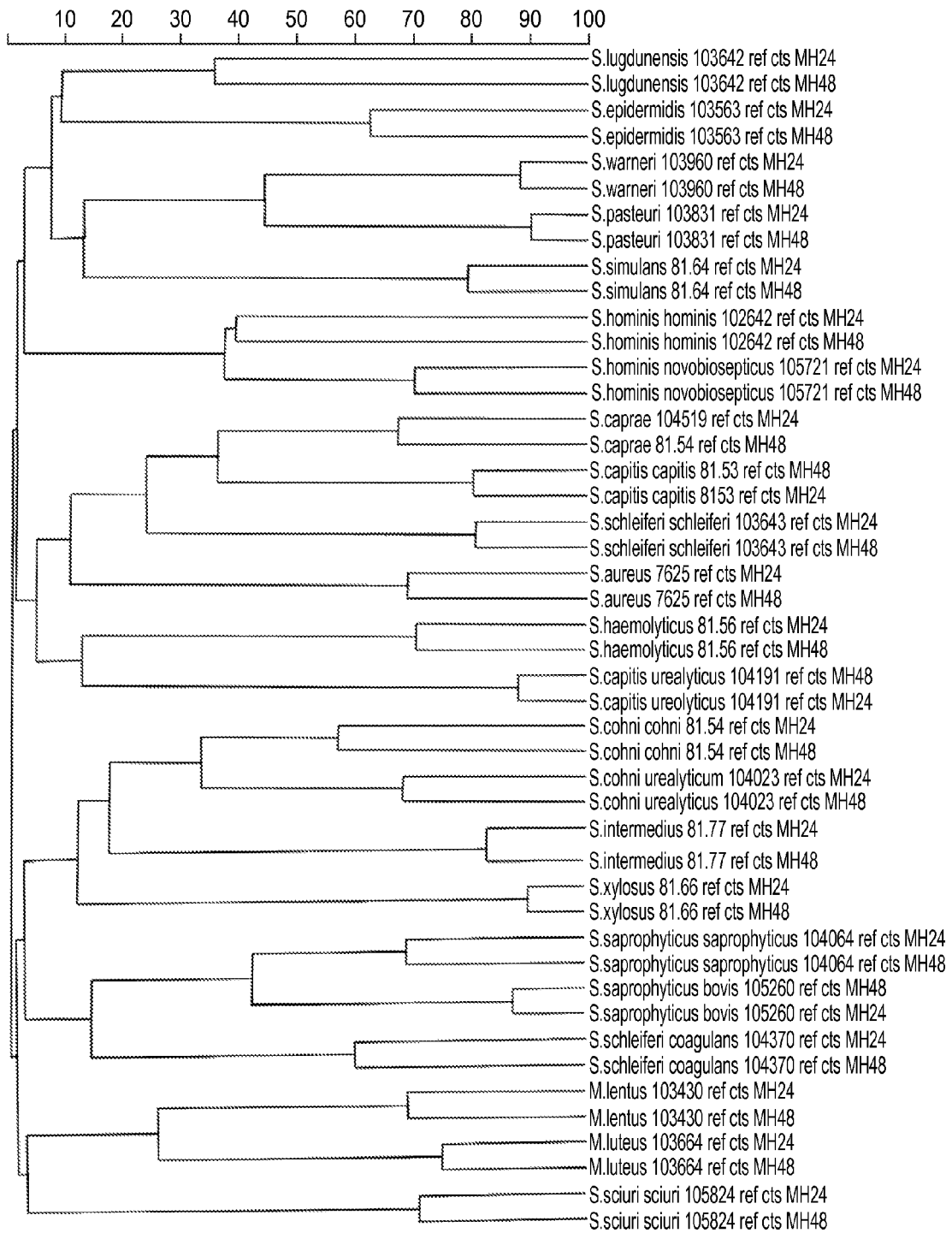
Figure 7:
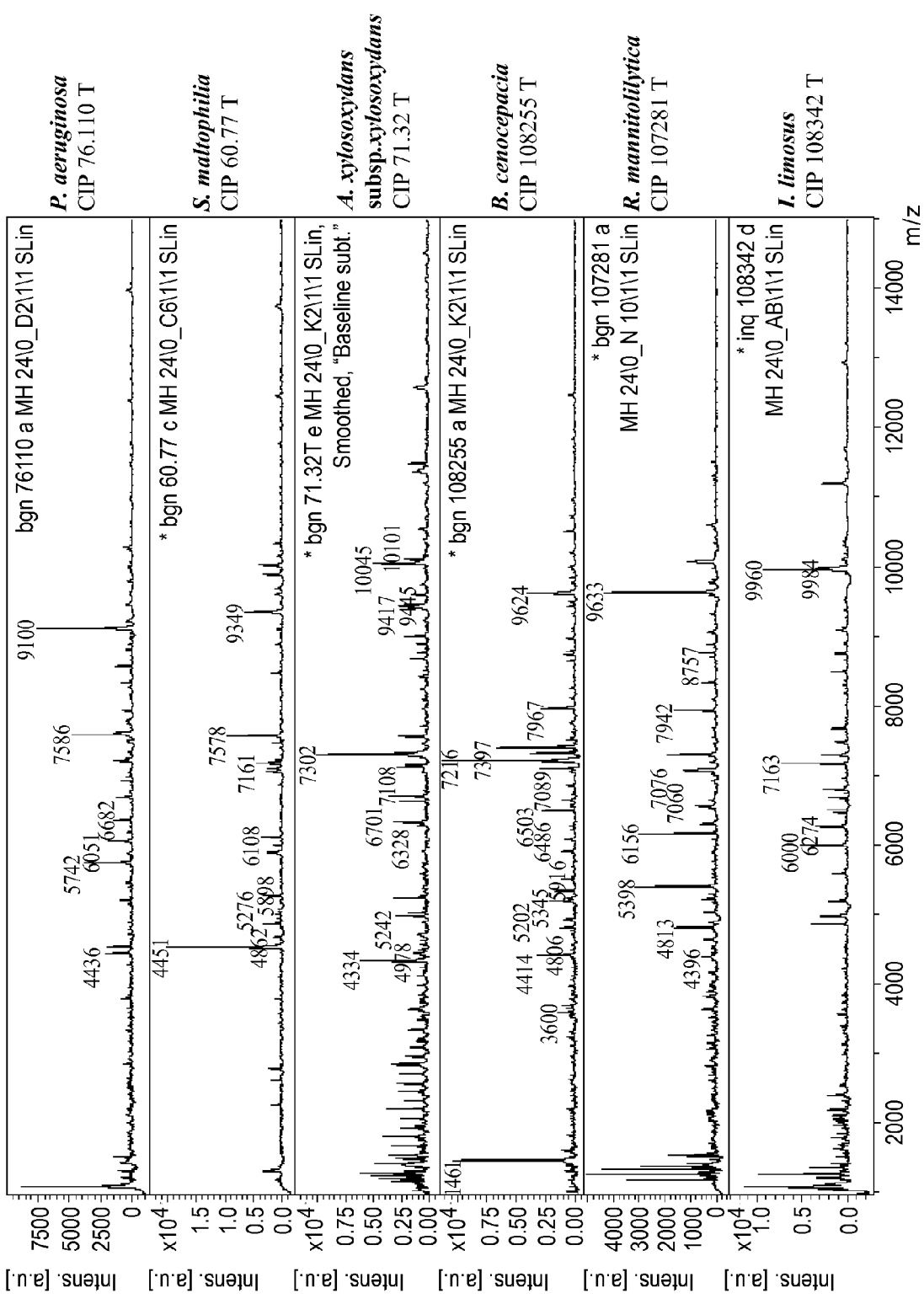

Other characteristics and advantages of the invention are given hereinafter with respect to the identification of 1) CNS at a species level, 2) non fermenting Gram negative *bacilli* isolated in cystic fibrosis, 3) yeasts and 4) molds. They are given to illustrate the invention without limiting its scope. It will be therein referred to FIGS. 1 to 7, which represent, respectively:

FIG. 1: MALDI-TOF-MS profiles of 10 isolates of the same strain of *S. aureus* CIP 7625;

FIG. 2: MALDI-TOF-MS dendrograms of *Micrococcacae* species, according to databases 1 (Muëller Hinton 24H) and 2 (Muëller Hinton 48H), thus designating the genospecies to be identified in this group of germs;

FIG. 3: m/z value of the peaks with a relative intensity above 0.1, concerning *Staphylococci* strains;

FIGS. 4 and 5: conservation of the set of peaks of selected strains among strains belonging to the same genospecies;

FIG. 6: aerobic and facultative anaerobic bacteria classification;

FIG. 7: MALDI-TOF-MS profiles of 6 Gram negative *bacilli*.

1. Identification of CNS at a Species Level

Material and Methods
Bacterial Strains

The results given hereinafter were obtained by analysing fifty one strains of bacteria belonging to the *Micrococcaceae* obtained from the collection of Institut Pasteur (CIP) (Paris, France).

The selected strains used to establish the MALDI-TOF-MS databases are given in Table 1

TABLE 1

| species | Strain |
|---|---|
| Staphylococcus aureus | CIP 7625 |
| Micrococcus luteus | CIP 103664 |
| M. lentus | CIP 103430 |

TABLE 1-continued

| species | Strain |
|---|---|
| S. epidermidis | CIP 103563 |
| S. warneri | CIP 103960 |
| S. xylosus | CIP 8166 |
| S. intermedius | CIP 8177 |
| S. haemolyticus | CIP 81.56 |
| S. saprophyticus subsp saprophyticus | CIP 104064 |
| S. saprophyticus subsp bovis | CIP 105260T |
| S. lugdunensis | CIP 103642 |
| S. hominis subsp hominis | CIP 102642 |
| S. hominis subsp novobiosepticus | CIP 105721 |
| S. capitis subsp capitis | CIP 8153T |
| S. capitis subsp ureolyticus | CIP 104191 |
| S. caprae | CIP 104519 |
| S. pasteuri | CIP 103831 |
| S. cohni subsp cohni | CIP 8154T |
| S. cohni subsp urealyticum | CIP 104023 |
| S. scheiferi subsp scheiferi | CIP 103643T |
| S. scheiferi subsp coagulans | CIP 104370 |
| S. sciuri subsp sciuri | CIP 103824 |
| S. simulans | CIP 8164 T |

The strains belonging to the Micrococcacae family are given in Table 2.

TABLE 2

| Species | Strain |
|---|---|
| S. aureus | 68 clinical isolates |
| M. luteus | CIP A270 |
| S. epidermidis | 81 clinical isolates |
| S. warneri | CIP 106511 |
|  | CIP 8165 |
|  | 6 clinical isolates |
| S. xylosus | CIP 103720 |
|  | CIP 104065 |
| S. intermedius | CIP 81.60 |
| S. haemolyticus | CIP 104114 |
|  | 13 clinical isolates |
| S. saprophyticus subsp saprophyticus | CIP 76.125T |
|  | CIP 103545 |
| S. saprophyticus subsp bovis | CIP 105262 |
|  | CIP 105261 |
| S. saprophyticus spp* | 6 clinical isolates |
| S. lugdunensis | CIP 103584 |
| S. hominis subsp hominis | CIP 81.57 |
|  | CIP 104689 |
| S. hominis subsp novobiosepticus | CIP 105719T |
| S. hominis spp* | 10 clinical isolates |
| S. capitis subsp capitis | CIP 103688 |
| S. capitis subsp ureolyticus | CIP 104192T |
| S. caprae | CIP 104000T |
|  | CIP 104520 |
| S. pasteuri | CIP 105540T |
|  | CIP 103830 |
|  | CIP 103832 |
| S. cohni subsp urealyticum | CIP 104024T |
|  | CIP 104025 |
| S. scheiferi subsp coagulans | CIP 104366 |
| S. sciuri subsp sciuri | CIP 8162T |
|  | CIP 103583 |
|  | CIP 103825 |

*the genospecies of these clinical strains were identified using the sequence of the sodA gene which does not discriminate between the 2 subspecies One hundred and sixteen clinical coagulase negative *Staphylococci* (CNS) isolates were also studied: 74 strains isolated from blood cultures, 25 strains isolated from children mediastinitis (skin, mediastinal liquid, electrodes), 12 strains isolated from bone infections (Hôpital Necker-Enfants malades, Paris; Hôpital Raymond Poincaré, Garches, France), and 5 strains isolated from urinary tract infections. In addition, 68 clinical strains of *Staphylococcus aureus* isolated from miscellaneous infections were analyzed.

Phenotypic and Genotypic Identification

The clinical strains of CNS were differentiated from *S. aureus* strains by conventional phenotypic tests including Slidex latex agglutination test (BioMérieux, Marcy l'Etoile, France) and DNAse test. Tube coagulase tests were performed in case of discordance between the two latest techniques. The precise identification of the CNS was obtained by sequencing an internal fragment of the SodA gene as previously described. Briefly, extraction of genomic DNA from pure cultures of CNS was performed with Quiagene kit (Courtaboeuf, France). Partial SodA gene was amplified and the amplicons obtained were sequenced using ABI Big Dye Terminator v1.1 cycle sequencing ready reaction kit (Applied Biosystems, Foster City, Calif., USA) as previously described by Poyart et al. 2001, J. Clin. Microbiol. 39:4296-4301. The nucleotidic sequences were sent to the GenBank database for species assignment.

Using this strategy, the 116 clinical CNS isolates given in table 2 were identified.

MALDI-TOF-MS Technique

The strains were grown on Mueller Hinton agar or Columbia agar +5% horse blood (BioMérieux), incubated 24 or 48H at 37° C. For each identification, a isolated colony was harvested in 100 µl of sterile water; 1 µl of this mixture was deposited on a target plate (Bruker Daltonics, Bremen, Germany) in 3 replicates and allowed to dry at room temperature. One µl of absolute ethanol was then added in each well, and 1 µl of the matrix solution DHB (2.5 dihydroxybenzoic acid 50 mg/ml, acetonitrile 30%, trifluoroacetic acid 0.1%). After drying, 1 µl of the matrix solution DHB was added. Samples were then processed in the spectrometer MALDI-TOF-MS autoflex (Bruker Daltonics) with the flex control software (Bruker Daltonics). Positive ions were extracted with an accelerating voltage of 20 Hz in linear mode. Each spectrum was the sum of the ions from 5×200 laser shots coming from different regions of the same well, and was analyzed in a range from m/z 1000 to 23000. The analysis was performed with the flex analysis software and calibrated with the protein calibration standard T (Protein I, Bruker Daltonics). The data obtained with the 3 replicates were added to minimise random effect. The presence and absence of peaks were considered as fingerprints for a particular isolate. The profiles were analysed and compared using the software BGP-database available on the website http://sourceforge.net/projects/bgp.

Results

Strains listed in table 1 are those arbitrary selected as being representative of the genospecies.

Ten isolates of each of these selected strains were analyzed by MALDI-TOF-MS as described in the materials and methods section.

For each spectrum, a value corresponding to the intensity was given to each peak.

The peak with the highest intensity was arbitrarily set up to 1, all the other peaks had a value corresponding to the relative intensity of this highest peak (FIG. 1).

Minor peaks (relative intensity below 0.1) were inconstantly present. The analysis was then subsequently concentrated on peaks with a relative intensity above 0.1 that were present in all 10 sets of data obtained for a given strain.

In order to determine the impact of growth conditions on bacterial identification, the above described procedure was performed with all strains listed table 1 and grown on Mueller Hinton or Columbia agar supplemented with 5% horse blood for 24 or 48 hours.

The results are given in Table 3.

The databases were designated 1 through 4, respectively: they were obtained using bacterial cultures on Mueller Hinton 24H (database 1), Mueller Hinton 48H (database 2), columbia horse blood medium 24H (database 3), columbia horse blood medium 24H (database 4). For a given strain, the standard deviation of the m/z value for each of the conserved peak was never above 7. The m/z value of the peaks with a relative intensity above 0.1 and present in all 10 sets of data for each growth condition are reported on FIG. 3.

TABLE 3

Number of peaks for each database*

| | database 1 | database 2 | database 3 | database 4 | | database 1 | database 2 | database 3 | database 4 |
|---|---|---|---|---|---|---|---|---|---|
| S. aureus | 11 | 11 (8) | 7 (2) | 8 (4) | S. intermedius | 10 | 12 (9) | 7 (6) | 6 (5) |
| S. capitis capitis | 8 | 14 (7) | 4 (4) | 6 (4) | S. lugdunensis | 9 | 12 (5) | 5 (3) | 9 (4) |
| S. capitis urealyticus | 5 | 9 (4) | 6 (3) | 4 (4) | S. pasteuri | 11 | 12 (11) | 10 (10) | 12 (9) |
| S. caprae | 5 | 12 (5) | 6 (2) | 6 (2) | S. saprophyticus bovis | 9 | 12 (8) | 7 (2) | 5 (3) |
| S. cohni cohni | 6 | 9 (4) | 10 (2) | 11 (5) | S. saprophyticus saprophyticus | 8 | 10 (6) | 7 (4) | 11 (4) |
| S. cohni urealyticum | 6 | 12 (6) | 7 (4) | 8 (5) | S. schleiferi coagulans | 7 | 8 (6) | 4 (4) | 10 (5) |
| S. epidermidis | 4 | 11 (4) | 4 (2) | 6 (2) | S. schleiferi schleiferi | 9 | 10 (9) | 5 (5) | 9 (5) |
| S. haemolyticus | 5 | 10 (5) | 4 (4) | 8 (4) | S. sciuri sciuri | 8 | 11 (8) | 3 (1) | 4 (3) |
| S. hominis hominis | 8 | 9 (4) | 4 (4) | 5 (3) | S. simulans | 8 | 8 (7) | 4 (5) | 110 (7) |
| S. hominis novobiosepticus | 6 | 12 (6) | 8 (2) | 8 (3) | S. warneri | 9 | 13 (6) | 10 (7) | 14 (6) |
| S. intermedius | 10 | 12 (9) | 7 (6) | 6 (5) | S. xylosus | 5 | 9 (4) | 8 (4) | 9 (4) |
| M. lentus** | 3 | 7 (3) | | | M. luteus | 6 | 13 (4) | 10 (4) | 13 (6) |

*number in brackets is the number of common peaks with those of database 1
**M. lentus did not grow on horse blood medium Table 3 shows for each selected strain and each database the number of peaks that have been retained. Whereas for a strain, some peaks were conserved regardless of the medium or the time of culture, other peaks either disappeared or appeared upon changing culture conditions. However, for a given medium and time of culture, the set of peaks was strain specific as showed on dendrograms (FIG. 2).

Conservation of the Set of Peaks of Each Selected Strains Among Strains Belonging to the Same Genospecies To address this point, MALDI-TOF MS was performed using bacteria grown on Mueller Hinton for 24 hours at 37° C. The strains used are the isolates listed table 2.

For each strain, the sole peaks with a value above 0.1 were retained. The profile obtained was then compared for each of these isolates with that of those of database 1.

To perform this task, a software (BGP-database available on http://sourceforge.net/projects/bgp) was developed allowing the rapid identification of the closest set of values in the database with that of the tested strain. This software chooses the best match between the tested strain and the reference strains of the database taking into account a possible error of the m/z value that has been measured. This value was arbitrarily set up to 7.

The tested strain had always the best match with the strain belonging to the same genospecies of the database. All data are reported on FIG. 4 and FIG. 5.

Average Number of Conserved Peaks of the Tested Strains Cultivated According on Mueller Hinton for 24H Compared to the Number of Peaks of Each Database The same set of data obtained by growing the tested bacteria on Mueller Hinton during 24 hours was tested against databases 2, 3 and 4.

The results are given in table 4.

TABLE 4

| Species | Number of strains | database 1 | database 2 | database 3 | database 4 |
|---|---|---|---|---|---|
| S. aureus | 68 | 9.6/11 | 8.7/11 | 4.5/7 | 4.7/8 |
| S. capitis capitis | 1 | 8/8 | 14/14 | 4/4 | 6/6 |
| S. capitis urealyticus | 1 | 7/7 | 7/9 | 6/6 | 4/4 |
| S. caprae | 2 | 5/5 | 8/12 | 6/6 | 5/6 |
| S. cohni urealyticus | 2 | 6/6 | 9/12 | 7/7 | 6.5/8 |
| S. epidermidis | 81 | 3.2/4 | 5.1/11 | 2.2/4 | 3.4/6 |
| S. haemolyticus | 14 | 3.4/5 | 5.4/10 | 3.3/4 | 4.8/8 |
| S. hominis hominis | 6 | 5.6/8 | *5.7/9 | 3.5/4 | 3.6/5 |
| S. hominis novobio | 7 | 4/6 | *7.7/12 | ***2.7/7 | *****3.1/8 |
| S. intermedius | 1 | 10/10 | 11/12 | 7/7 | 6/6 |
| S. lugdunensis | 1 | 8/8 | 11/12 | 5/5 | 9/9 |
| S. saprophyticus bovis | 3 | 7.6/9 | 9.6/12 | ****4/7 | 4/5 |
| S. saprophyticus saprophyticus | 7 | 6/8 | **5.8/10 | 5.1/7 | 8/11 |
| S. schleiferi coagulans | 1 | 7/7 | 6/8 | 4/4 | 10/10 |
| S. pasteuri | 3 | 11/11 | 11/12 | 9.5/10 | 11.6/12 |
| S. sciuri sciuri | 3 | 7/7 | 8.3/11 | 2.3/3 | 3.6/4 |
| S. xylosus | 2 | 5/5 | 9/9 | 7/8 | 6/9 |

TABLE 4-continued

| Species | Number of strains | database 1 | database 2 | database 3 | database 4 |
|---|---|---|---|---|---|
| S. warneri | 8 | 6.7/9 | 8.8/10 | 8/10 | 6.8/14 |
| M. luteus | 1 | 7/7 | 11/12 | 8/10 | 11/11 |

*One strain could not be differentiated be identified at the subspecies level
**3 S. saprophyticus bovis identifications
***6 S. hominis hominis identifications
****1 S. saprophyticus saprophyticus identifications
*****3 strains not differentiated between S. hominis hominis and S. hominis novobiosepticus Table 4 shows for each genospecies the average number of peaks that were conserved between the tested strains and each of the four databases.

Even though the number of peaks that were conserved when the databases used for the genospecies identification were established using different growth conditions from those used for the tested strains, in all cases the identification at the species level was possible.

The only difference observed by using databases 2, 3 and 4 with those obtained with database 1, is that the identification at the subspecies level was impossible for S. hominis and S. saprophyticus unlike results obtained with database 1.

Altogether, said data demonstrate that by selecting an appropriate set of strains and retaining only the conserved peaks with a m/z above 0.1 a database that can be used for genospecies identification can be engineered. Furthermore the specificity of these peaks is such that genospecies identification remained possible even if the strains to be identified have been grown using different culture conditions than those used to engineer the database.

2. Identification of Non Fermenting Gram Negative *Bacilli*

The first step was to build a complete database for all species belonging to the group of non fermenting Gram negative *bacilli* recovered in human. This database was then validated to identify using MALDI-TOF MS all the clinical non fermenting Gram negative *bacilli* that have been recovered from Cystic fibrosis (CF) patients in a one year period.

Material and Methods

Bacterial Strains

The reference strains used to engineer the MALDI-TOF MS database belong to 52 species of non fermenting Gram negative *bacilli* that can possibly be recovered from patients. These strains are listed Table 4.

TABLE 4

| Species | Reference strain | Species | Reference strain |
|---|---|---|---|
| Pseudomonas aeruginosa | CIP 76.110 | Inquilinus limosus | CIP 108342 T |
| Pseudomonas fluorescens | CIP 69.13 T | Pandoraea apista | CIP 106627 T |
| Pseudomonas mosselii | CIP 104061 | Bordetella avium | CIP 103348 T |
| Pseudomonas putida | CIP 52.191 T | Bordetella bronchiseptica | CIP 55.110 T |
| Pseudomonas stutzeri | CIP 103022 T | Bordetella hinzii | CIP 104527 T |
| Pseudomonas mendocina | CIP 75.21 T | Alcaligenes faecalis subsp. faecalis | CIP 60.80 T |
| Pseudomonas alcaligenes | CIP 101034 T | Aeromonas sobria | CIP 74.33 T |
| Pseudomonas pseudoalcaligenes | CIP 66.14 T | Aeromonas hydrophila subsp. hydrophila | CIP 76.14 T |
| Pseudomonas oryzihabitans | CIP 102996 T | Aeromonas veronii | CIP 103438 T |
| Pseudomonas luteola | CIP 102995 T | Aeromonas caviae | CIP 76.16 T |
| Stenotrophomonas maltophilia | CIP 60.77 T | Delftia acidovorans | CIP 103021 T |
| Achromobacter xylosoxydans subsp. xylosoxydans | CIP 71.32 T | Shewanella putrefaciens | CIP 80.40 T |
| | | Plesiomonas shigelloides | CIP 63.5 T |
| Achromobacter xylosoxydans subsp. denitrificans | CIP 77.15 T | Chryseobacterium indologenes | CIP 101026 T |
| | | Elizabethkingia meningoseptica | CIP 60.57 T |
| Achromobacter piechaudii | CIP 60.75 T | Sphingobacterium multivorum | CIP 100541 T |
| Burkholderia cepacia | CIP 80.24 T | Sphingobacterium spiritivorum | CIP 100542 T |
| Burkholderia multivorans | CIP 105495 T | Brevundimonas diminuta | CIP 63.27 T |
| Burkholderia cenocepacia | CIP 108255 T | Brevundimonas vesicularis | CIP 101035 T |
| Burkholderia stabilis | CIP 106845 T | Sphingomonas paucimobilis | CIP 100752 T |
| Burkholderia vietnamlensis | CIP 105875 T | Cupriavidus pauculus | CIP 105943 T |
| Burkholderia dolosa | CIP 108406 | Inquilinus limosus | CIP 108342 T |
| Burkholderia ambifaria | CIP 107266 T | Pandoraea apista | CIP 106627 T |
| Burkholderia anthina | CIP 108228 T | Bordetella avium | CIP 103348 T |
| Burkholderia pyrrocinia | CIP 105874 T | Bordetella bronchiseptica | CIP 55.110 T |
| Burkholderia gladioli | CIP 105410 T | Bordetella hinzii | CIP 104527 T |
| Burkholderia gladioli pathovar cocovenenans | ATCC 33664 | Alcaligenes faecalis subsp. faecalis | CIP 60.80 T |
| | | Aeromonas sobria | CIP 74.33 T |
| Burkholderia glumae | NCPPB 2391 | Aeromonas hydrophila subsp. hydrophila | CIP 76.14 T |
| Burkholderia plantarii | ATCC 43733 | Aeromonas veronii | CIP 103438 T |
| Burkholderia glathei | CIP 105421 T | Aeromonas caviae | CIP 76.16 T |
| Burkholderia andropogonis | CIP 105771 T | Delftia acidovorans | CIP 103021 T |
| Ralstonia mannitolilytica | CIP 107281 T | | |
| Ralstonia pickettii | CIP 73.23 T | | |
| Cupriavidus gilardii | CIP 105966 T | | |
| Cupriavidus pauculus | CIP 105943 T | | |

The clinical isolates of non fermenting Gram negative *bacilli* were recovered from the sputum of CF children attending the pediatric department of the Necker-Enfants Malades hospital (Paris, France) between Jan. 1, 2006 and 31/12/06. Briefly, isolates displaying Green or Yellow-Green pigmentation, positive oxidase test, growth at 42° C., growth on cetrimide agar and susceptibility to colimycin were identified as *Pseudomonas aeruginosa*. Isolates which didn't express those criteria were identified by API 20NE system. The results of the API 20NE tests were interpreted using the APILAB PLUS software package. When the results obtained using this software were not considered as corresponding to a good identification for *P. aeruginosa, A. xylosoxydans* subsp. *xylosoxydans* and *S. maltophilia*, the bacteria were identified by sequencing an internal fragment of the 16S rDNA gene.

All bacterial strains used in the study were stored at −80° C. in trypticase soy broth supplemented with 15% glycerol.

MALDI-TOF-MS. The strains were grown on Mueller-Hinton agar and incubated for 24 h at 37° C. Most of the isolates grew after 24 h but some strains that didn't grow after 24 h were further incubated for 48 h or 72 h. An isolated colony was harvested in 100 μl of sterile water; 1 μl of this mixture was deposited on a target plate (Bruker Daltonics, Bremen, Germany) in three replicates and allowed to dry at room temperature. One microliter of absolute ethanol was then added in each well, and the mixture allowed to dry. One μl of matrix solution DHB (2,5-dihydroxybenzoic acid, 50 mg/ml, 30% acetonitrile, 0.1% trifluoroacetic acid) was then added. Samples were processed in the MALDI-TOF-MS spectrometer (Autoflex; Bruker Daltonics) with flex control software (Bruker Daltonics). Positive ions were extracted with an accelerating voltage of 20 kV in linear mode. Each spectrum was the sum of the ions obtained from 200 laser shots performed in five different regions of the same well. The spectra have been analyzed in an m/z range of 2,000 to 20,000. The analysis was performed with the flex analysis software and calibrated with protein calibration standard T (Protein I; Bruker Daltonics). The data obtained with the three replicates were added to minimize random effect. The presence and absence of peaks were considered as fingerprints for a particular isolate. The profiles were analyzed and compared using the newly developed software BGP database available on the website http://sourceforge.net/projects/bgp.

Results

Engineering of the Non Fermenting Gram Negative *Bacilli* Database

Reference strains listed Table 4 were used to determine the m/z values obtained by MALDI-TOF-MS that constitute a characteristic spectrum of each bacterial species and could then be used for bacterial identification. FIG. 7 shows the spectrum obtained with 6 species of non fermenting Gram negative *bacilli*. Ten isolates of each of these selected strains grown on Mueller Hinton 24H were analyzed by MALDI-TOF-MS as described in the material and methods section. For each spectrum, the same strategy as that used for *Micrococcacae* was adopted. According to this strategy, only those peaks with an intensity above 0.1 that were constantly present in all 10 sets of data obtained for a given strain were retained. For each strain, the m/z value of standard deviation (normalized data) for each conserved peak never exceeded 8.

Table 5 shows for 8 species the values of peaks that have been retained for the database.

TABLE 5

| *Achromobacter xyloxosidans xyloxosidans* CIP 71.32T | *Pseudomonas aeruginosa* CIP 76.110 | *Pseudomonas fluorescens* CIP 69.13T | *Pseudomonas putida* CIP 52.191 | *Burkholderia cenocepacia* CIP 108255 T | *Burkholderia gladioli* CIP 105410T | *Stenotrophomonas maltophilia* CIP 60.77T | *Ralstonia mannitolylitica* CIP 107281T |
|---|---|---|---|---|---|---|---|
| 1208 +/− 1 | 4436 +/− 2 | 4339 +/− 1 | 3810 +/− 1 | 3600 +/− 2 | 4416 +/− 1 | 4541 +/− 1 | 3818 +/− 3 |
| 1419 +/− 1 | 4544 +/− 3 | 6089 +/− 1 | 4439 +/− 1 | 4414 +/− 2 | 4808 +/− 1 | 4862 +/− 1 | 4396 +/− 1 |
| 2190 +/− 1 | 5213 +/− 3 | 6275 +/− 2 | 6089 +/− 1 | 4806 +/− 2 | 5204 +/− 1 | 5276 +/− 1 | 4813 +/− 4 |
| 2319 +/− 1 | 5742 +/− 3 | 6403 +/− 1 | 6275 +/− 1 | 5202 +/− 2 | 5225 +/− 3 | 5898 +/− 3 | 5398 +/− 4 |
| 2447 +/− 1 | 6051 +/− 3 | 6634 +/− 2 | 6403 +/− 2 | 5345 +/− 2 | 6305 +/− 1 | 6108 +/− 1 | 6156 +/− 4 |
| 2576 +/− 1 | 6353 +/− 3 | 7182 +/− 1 | 6634 +/− 2 | 5916 +/− 3 | 6489 +/− 2 | 7161 +/− 2 | 7060 +/− 5 |
| 2705 +/− 1 | 6682 +/− 4 | 7604 +/− 2 | 7182 +/− 2 | 6486 +/− 3 | 6597 +/− 1 | 7578 +/− 2 | 7078 +/− 5 |
| 2833 +/− 1 | 6918 +/− 4 | 7647 +/− 1 | 7604 +/− 2 | 6503 +/− 4 | 6859 +/− 2 | 9349 +/− 2 | 7943 +/− 4 |
| 2865 +/− 1 | 7211 +/− 4 | 9568 +/− 1 | 7647 +/− 2 | 7089 +/− 3 | 6959 +/− 2 | | 9632 +/− 4 |
| 2962 +/− 1 | 7586 +/− 4 | | 9568 +/− 2 | 7216 +/− 3 | 7060 +/− 2 | | |
| 4334 +/− 1 | 7621 +/− 4 | | | 7318 +/− 3 | 7105 +/− 2 | | |
| 4978 +/− 1 | 8575 +/− 5 | | | 7397 +/− 3 | 7185 +/− 2 | | |
| 5018 +/− 1 | 9100 +/− 5 | | | 7967 +/− 3 | 7217 +/− 3 | | |
| 5242 +/− 1 | | | | 9624 +/− 4 | 7325 +/− 2 | | |
| 6328 +/− 2 | | | | | 7673 +/− 1 | | |
| 6701 +/− 2 | | | | | 7794 +/− 2 | | |
| 7108 +/− 1 | | | | | 8737 +/− 2 | | |
| 7302 +/− 1 | | | | | 9627 +/− 2 | | |
| 9417 +/− 2 | | | | | 10458 +/− 4 | | |
| 9445 +/− 2 | | | | | | | |
| 10045 +/− 2 | | | | | | | |
| 10101 +/− 2 | | | | | | | |

The set of peaks retained for each reference strain gives a characteristic spectrum.

Identification of the Clinical Strains

Experiments were carried out to determine whether the above databases could be used for the identification of clinical non fermenting Gram negative *bacilli*, thus demonstrating that the set of peaks of each selected strain is, at least partially, conserved among isolates of the same species. From January to December 2006, 811 strains of non fermenting Gram negative *bacilli* were recovered and identified by phenotypical tests or molecular method: 699 *P. aeruginosa* strains (120 patients) 54 *A. xylosoxydans* (12 patients), 32 *S. maltophilia* (12 patients), 9 *R. mannitolilytica* (1 patient), 14 Bcc (2 patients), 1 *B. gladioli,* 1 *B. hinzii* and 1 *I. limosus*. Of these, MALDI-TOF-MS analysis was performed on a panel of 400 *P. aeruginosa* strains and on all remaining non *P. aeruginosa* strains. For each isolate, all m/z values of the spectrum were considered. For each strain, all peaks were retained regardless of their intensity and were then compared with that of the database using the BGP-database software. This software chooses the best match between the tested strain and the database, taking into account a possible error of the m/z value. This value was set up to 10. The strain was identified as belonging to the genospecies of the strain of the database giving the best match. The results are given in Table 6 below which shows the matches obtained for a P. aeruginosa strain provided by the BGP software.

TABLE 6

Profile Name: P. aeruginosa
Match: 13/13

| 06178603.0, txt values | P. aeruginosa values |
|---|---|
| 4441 | 4436 |
| 4548 | 4544 |
| 5216 | 5213 |
| 5743 | 5742 |
| 6053 | 6051 |
| 6354 | 6353 |
| 6682 | 6682 |
| 6917 | 6918 |
| 7209 | 7211 |
| 7584 | 7586 |
| 7620 | 7621 |
| 8571 | 8575 |
| 9096 | 9100 |

Profile Name: F. orzyhabitans
Match: 7/12

| 06178603.0, txt values | F. orzyhabitans values |
|---|---|
| 4441 | 4435 |
| 6053 | 6053 |
| 6505 | 6503 |
| 6682 | 6680 |
| 7497 | 7498 |
| 7584 | 7581 |
| 9123 | 9126 |

Table 7 shows the identification obtained for all clinical strains, compared to the second choice of species identification.

MALDI-TOF-MS correctly identified 100% of P. aeruginosa, 100% of A. xylosoxydans and 100% of S. maltophilia strains. MS identified A. xylosoxydans clinical strains at the subspecies level. MS analysis correctly identified 11 BCC strains as B. cenospacia. For the remaining 3 BCC strains, there was no differentiation between B. cenocepacia and B. cepacia sensu stricto. It should pointed out that the 9 R. mannitolilytica strains except one (identified by MS as R. picketti) were correctly identified by MS.

Conclusion

These results demonstrate that the database engineered according to the invention is also suitable for accurate species identification of non fermenting Gram negative bacilli. With MALDI-TOF-MS, it is thus possible, from one colony of non fermenting Gram negative bacilli (culture conditions, characteristics of the colony), to obtain within minutes a precise identification without additional test. The tested CF clinical strains were accurately identified at the species level except for three B. cenocepacia strains and one R. mannitolylitica. It is interesting to note that the strain identified as B. gladioli matched also with the reference strain of B. cocovenenans, a bacterial species that has been shown to be a junior synonym of B. gladioli.

MALDI-TOF-MS enables very rapid bacterial identification while conventional biochemical identification by API 20NE often requires more than 24 h-48 h with frequent misidentifications. MALDI-TOF-MS strains identification is therefore a very interesting method for characterization of Gram negative bacilli species and will help understanding their clinical relevance and distribution.

3. Identification of Candida and Saccharomyces at the Species Level

Material and Methods
Yeast Strains.

The reference strains used to engineer the MALDI-TOF MS database belonged to 19 clinically relevant species of Candida, which have been involved in human pathology. The tested strains used to validate the databases were 148 clinical

TABLE 7

| Strains (number) | Patients (number) | Species identified by conventional technics | Comparison with the reference strain | | Difference of % of common peaks with respective reference strains between the first and the second choice of species |
|---|---|---|---|---|---|
| | | | Reference strain | Mean % of common peaks | |
| 400 | 100 | P. aeruginosa | P. aeruginosa | 86 (ext: 23-100) | 35 (ext: 2-67) |
| 54 | 11 | A. xylosoxydans subsp. xylosoxydans | A. xylosoxydans subsp. xylosoxydans | 91 (ext: 73-100) | 75 (ext: 1-5) (2$^{nd}$ choice: mostly A. piechaudii or A. xylosoxydans subsp. denitrificans) |
| 32 | 12 | S. maltophilia | S. maltophilia | 82 (ext: 63-100) | 36 (ext: 4-59) |
| 14 | 2 | B. cepacia* complex | B. cenocepacia | 89 (ext: 71-100) | 23 (ext: 2-31) |
| 9 | 1 | Ralstonia spp** | R. mannitolilytica | 76 (ext: 60-80) | 8 (ext: 2-18) |
| 1 | 1 | B. gladioli | B. gladioli | 78*** | 14*** |
| 1 | 1 | B. hinzii | B. hinzii | 90 | 34 |
| 1 | 1 | I. limosus | I. limosus | 60 | 35 |

*All strains except 3(identified as B. cepacia sensu stricto) were correctly identified as B. cenocepacia.
**All strains but one (identified as R. picketti) were correctly identified as R. mannitolilytica.
***this percentage is the same as that obtained with B. gladioli pathovar. cocovenenans isolates of *Candida* belonging to 19 species: 25 *C. albicans*, 3 *C. dubliniensis*, 25 *C. glabrata*, 3 *C. nivariensis*, 20 *C. tropicalis*, 25 *A. parapsilosis*, 1 *C. orthopsilosis*, 6 *C. krusei*, 3 *C. guillermondii*, 1 *C. haemulonii*, 7 *C. kefyr*, 3 *C. pelliculosa*, 3 *C. lipolytica*, 2 *C. norvegensis*, 4 *C. inconspicua*, 1 *C. lamblica*, 7 *C. lusitaniae*, 1 *C. sphaerica*, 2 *C. rugosa*, 4 *S. cerevisiae*. All strains were identified by phenotypical methodologies (Auxacolor, ID32C BioMerieux) or by Internal Transcribed spacer (ITS) sequencing. All *Candida* strains used in the study were stored at −80° C. in trypticase soy broth supplemented with 15% glycerol.

*C. albicans* isolates belonging to the 17 ever well-described clades were chosen to identify different patterns of spectra within the *C. albicans* species, in order to be able to discriminate them each other and with other species. Indeed, *C. albicans* population is complex and can be divided in 17 genetical sub-populations using MLST method. Each clade has homogeneous genetical characteristics.

Some species included in the databases cannot be identified with current phenotypical methodology, but only with molecular identification based on ITS or D1/D2 sequencing.

Hence routine classical identification *C. nivariensis* and *C. bracanensis* cannot discriminate from *C. glabrata*, *C. famata* and *C. fermantati* from *C. guillermondii*, *C. orthopsilosis* and *C. metapsilosis* from *C. parapsilosis*.

Engineering of the Database.

Clinical identification of *Candida* species in clinical samples is performed from different media, in particular Sabouraud dextrose agar and different chromogenic media able to discriminate several species among the color of the colony. 3 databases were constructed for each reference strain, one based on Sabouraud dextrose agar media (Biorad), one on CANDI2 (BioMerieux) and the third on CHROMAGAR. Discriminating peaks selected and included in the databases were obtained from 10 independent passages of each strain. MALDI-TOF-MS.

The strains were grown on CANDI2 medium and incubated at 37° C. for 24 hours. One colony was collected with a 1 microliter hoese and mixed in 1 μl of 70% formic acid previously deposited on a target plate in triplicate (Bruker Daltonics, Bremen, Germany). This mixture allowed to dry at room temperature. One microliter of matrix solution SA (sinapinic acid, 10 mg/l, 30% acetonitrile, 0.1% trifluoroacetic acid) was then added and allowed to co-cristallize with the sample. Samples were processed in triplicates in the MALDI-TOF-MS spectrometer (Microflex, Bruker Daltonics) with the flex control software (Bruker Daltonics). Positive ions were extracted with an accelerating voltage of 20 kV in linear mode. The analysis was performed with the flex analysis software and calibrated with protein calibration standard I (Bruker Daltonics). The presence and absence of peaks were considered as fingerprints for a particular isolate. The profiles were analyzed and compared using the newly developed software BGP. Numerical data obtained from the spectrometer acquisition software (peak value and relative intensity for each peak) are sent to the BGP software. This software identifies the number of common peaks between the spectra of the tested strain and each set of peaks specific of a reference strain contained in the database (i.e *Candida* database). The software determines a percentage for each reference strain (100× number of common peaks between the tested strain and the peaks specific of one reference strain/total number of peaks specific of one reference strain). The identification of the tested strain corresponds to the species of the reference strain having the greater number of peaks after adding each peak of each specie of the first, second and third matches. The greater the difference between the first and second match, the better is the discrimination between species. A difference of at least 10% is required to obtain a good identification.

Results

The set of reference strains has been selected as belonging to clinically relevant *Candida* species and is given in Table 8 below:

TABLE 8

| Species (n = 21) | Reference strains |
| --- | --- |
| C. albicans | ATCC 900028, SC5314 |
| C. glabrata | ATCC 2001 |
| C. parapsilosis | ATCC 22019 |
| C. tropicalis | ATCC 750 |
| C. krusei | ATCC 6259 |
| C. guillermondii | ATCC 387 |
| C. nivariensis | NIV1* |
| C. orthopsilosis | ORT1* |
| C. haemulonii | HAE1* |
| C. kefyr | KEF2* |
| C. pelliculosa | PEL1* |
| C. lipolytica | LIP1* |
| C. norvegensis | NOR1* |
| C. inconspicua | INC2, NOR2* |
| C. lamblica | LAM1* |
| C. lusitaniae | LUS 5* |
| C. sphaerica | SPH1* |
| C. rugosa | RUG2* |
| S. cerevisiae | CER1* |
| C. neoformans var. grubii | H99 |

Ten passages of each of these selected strains grown on Sabouraud agar with chloramphenicol were analyzed by MALDI-TOF-MS as described in the material and methods section. For each strain, only those peaks with a relative intensity above 0.07 that were constantly present in all 10 sets of data obtained for a given strain were retained. The standard deviation for each conserved peak did not exceed 10 m/z value. The set of peaks was specific of each selected strain.

The results are given in Table 9 hereinafter

TABLE 9

| Species | Number of strains | Correct identification (%) |
| --- | --- | --- |
| C. albicans | 25 | 25/25 (100%) |
| C. glabrata | 25 | 25/25 (100%) |
| C. krusei | 6 | 5/6 (83%) |
| C. guillermondii | 3 | 3/3 (100%) |
| C. nivariensis | 3 | 3/3 (100%) |
| C. orthopsilosis | 1 | 1/1 (100%) |
| C. haemulonii | 1 | 1/1 (100%) |
| C. kefyr | 7 | 7/7 (100%) |
| C. pelliculosa | 3 | 3/3 (100%) |
| C. lipolytica | 3 | 3/3 (100%) |
| C. norvegensis | 2 | 2/2 (100%) |
| C. inconspicua | 4 | 4/4 (100%) |
| C. lamblica | 1 | 1/1 (100%) |
| C. lusitaniae | 7 | 6/7 (85%) |
| C. sphaerica | 1 | 1/1 (100%) |
| S. cerevisiae | 4 | 4/4 (100%) |
| 19 | 144 | 128/144 (88%) |

Experiments were then carried out to demonstrate that the set of peaks of each selected strain is, at least partially, conserved among isolates of the same species. The database was tested using the set of strains described in the material and methods section. For each isolate, all peaks with intensity >0.01 were retained and were compared with that of the specific peaks of each reference strain included in the database using the BGP-database software, taking into account a possible error of +/−10 m/z value. The percentage of common peaks obtained with each of the reference strains was next analyzed for all 144 tested strains identified with phenotypical identification. Only the first and second best matches were retained. Acceptable identification of a tested strain corresponds to the species having ≧66 of common peaks with the reference strains in the database. A difference of at least 10% between the first and the second match is required.

Using the database of the invention, identification was correct in over 98% of the cases.

4. Identification of *Aspergilli* at the Species Level

Materials and Methods
*Aspergillus* Strains

The reference strains used to engineer the MALDI-TOF MS database belonged to 28 clinically relevant species of *Aspergillus*, which have been involved in human pathology (Table 10 hereinbelow). The tested strains used to validate the databases were 120 clinical and 16 environmental isolates of *Aspergillus* belonging to 7 sections: 50 *A. fumigatus*, 7 *A. lentulus*, 5 *Neosartorya pseudofischeri*, 2 *A. viridinutans*, *A. fumigatiaffinis* and *A. hiratsukae*, 1 *A. fumisynnematus*, *N. fischeri* and *N. udagawae* (section Fumigati); 13 *A. flavus*, 2 *A. tamarii*, 1 *A. parvisclerotigenus* (section Flaw); 8 *A. terreus* (section Terre); 9 *A. niger*, 2 *A. foetidus*, 1 *A. tubengensis* (section Nigri); 4 *Emericella nidulans*, 1 *E. quadrilineata*, 7 *A. sydowii*, 3 *A. versicolor* (section Nidulantes); 11 *A. calidoustus*, 1 *A. pseudodeflectus*, 1 *A. insuetus* (section Usti); 1 *A. ochraceus* (section Ochracei). All strains were cultured on Sabouraud agar with chloramphenicol and gentamicin (Bio-Rad, Marnes-la-coquette, France). Clinical and environmental isolates were identified by molecular method based on multilocus sequencing using betatubulin and/or calmodulin genes. All the strains used in the study were stored at −80° C. in trypticase soy broth supplemented with 15% glycerol.

Construction of the Database.

A maturation of spores occurred during *Aspergillus* growth. For all references strains, 2 databases were constructed: one from early spores (less than 2 days of sporulation) and the other one from mature spores (more than 4 days of sporulation). 2 slow-sporulating reference strains (*A. fumisynnematus* and *A. ochraceus*) were included in only one reference database. Discriminating peaks selected and included in the databases were obtained from 10 independent passages of each strain.

MALDI-TOF-MS.

The strains were grown at 30° C. on Sabouraud dextrose Agar with chloramphenicol and gentamicin (Biorad, Marnes la coquette) and checked daily for consequent sporulation. Conidiophores and/or spores were collected gently at the surface of the colony and mixed in 1 µl of sterile water previously deposited on a target plate (Bruker Daltonics, Bremen, Germany). This mixture was allowed to dry at room temperature. One µl of absolute ethanol was then added in each well, and the mixture allowed to dry. One µl of matrix solution DHB (2,5-dihydroxybenzoic acid, 50 mg/ml, 30% acetonitrile, 0.1% trifluoroacetic acid) was then added and allowed to co-cristallize with the sample. Samples were processed in duplicates in the MALDI-TOF-MS spectrometer (Microflex, Bruker Daltonics) with the flex control software (Bruker Daltonics). Positive ions were extracted with an accelerating voltage of 20 kV in linear mode. The analysis was performed with the flex analysis software and calibrated with protein calibration standard I (Bruker Daltonics). The presence and absence of peaks were considered as fingerprints for a particular isolate. The profiles were analyzed and compared using the newly developed software BGP. Numerical data obtained from the spectrometer acquisition software (peak value and relative intensity for each peak) are sent to the BGP software. This software identifies the number of common peaks between the spectra of the tested strain and each set of peaks specific of a reference strain contained in the database (i.e *Aspergilli* database). The software determines a percentage for each reference strain (100× number of common peaks between the tested strain and the peaks specific of one reference strain/total number of peaks specific of one reference strain). The identification of the tested strain corresponds to the species of the reference strain having at least 66% of common peaks with the tested strain in the database. A difference of at least 10% between the first and the second match is required to obtain a correct identification. If the identification is not acceptable after one passage (ie <66% of common peaks with reference strain or <10% of difference between first and second matches), a second run was performed.

Results

A set of 28 reference strains (CBS or IHEM) have been selected as belonging to clinically relevant *Aspergillus* species They are given in Table 10 below which gives the reference strains used to establish the *Aspergilli* database.

| Section | Species | Reference strains |
|---|---|---|
| Fumigati (n = 11) | *A. fumigatus* | IHEM 1246 |
| | *A. lentulus* | CBS 116879 |
| | *Neosartorya pseudofischeri* | CBS 208.92 |
| | *N. fischeri* | IHEM 660 |
| | *A. fumigatiaffinis* | CBS 117194 |
| | *A. fumisynnematus* | CNM-CM-4063* |
| | *A. viridinutans* | CBS 127.56 |
| | *N. udagawae* | CBS 114217 |
| | *N. hiratsukae* | CBS 109356 |
| | *N. spinosa* | CBS 483.65 |
| | *N. fennelliae* | CBS 598.74 |
| Flavi (n = 5) | *A. flavus* | IHEM 306, IHEM 351 |
| | *A. oryzae* | CBS 115.33 |
| | *A. tamarii* | FLA 17* |
| | *P. alliaceus* | CBS 536.65 |
| | *A. parvisclerotigenus* | ASPSP SL 03* |
| Terrei (n = 1) | *A. terreus* | IHEM 5857 |
| Nigri (n = 3) | *A. niger* | IHEM 2864 |
| | *A. tubengensis* | NIG 11* |
| | *A. foetidus* | NIG 15* |
| Nidulantes (n = 4) | *Emericella nidulans* | IHEM 3665 |
| | *E. quadrilineata* | CBS 426.77 |
| | *A. sydowii* | IHEM 566 |
| | *A. versicolor* | IHEM 2983 |
| Usti (n = 3) | *A. calidoustus* | CBS 121601, IHEM 659 |
| | *A. pseudodeflectus* | ASPSP 26* |
| | *A. insuetus* | CNRMA F1-79* |
| Circumdati (n = 1) | *A. ochraceus* | OCH 1* |

IHEM: Institut scientifique de santé publique, BCCM-IHEM collection, Brussels, Belgium
CBS: Centraalbureau voor Schimmelcultures, Utrecht, the Nederlands
CNM-CM: Centro Nacional de Microbiologia-Servicio de Micologia, Madrid, Spain
*Reference spectra established with clinical isolates The set of peaks was specific of each selected reference strain. For each strain, only those peaks with a relative intensity above 0.01 that were constantly present in all 10 sets of data obtained for a given strain we retained the standard deviation for each conserved peak did not exceed 10 m/z value.

It was then determined whether the above database could be used for the identification of *Aspergillus* species, thus demonstrating that the set of peaks of each selected strain is, at least partially, conserved among isolates of the same species.

The database was tested using the set of 120 clinical and 16 environmental *Aspergillus* isolates. The characteristics of the 136 isolates of *Aspergillus* used in this study are given in Table 11. Species identification of each strain was obtained by sequencing betatubulin and/or calmodulin gene as shown in said Table.

TABLE 11

| Isolates number | | Specie | Section | Source | Geographical origin | GenBank Identification number (betatubulin) | GenBank Identification number (calmodulin) |
|---|---|---|---|---|---|---|---|
| OCH | 01 | A. ochraceus | Circumdati | Sputum | NEM, Paris, France | EF661322 | |
| FLA | 05 | A. flavus | | Sputum | NEM, Paris, France | EF661492 | |
| FLA | 07 | A. flavus | | Sputum | NEM, Paris, France | EF661492 | |
| FLA | 08 | A. flavus | | Sputum | NEM, Paris, France | AY017536 | |
| FLA | 10 | A. flavus | | Sputum | NEM, Paris, France | AY017536 | |
| FLA | 14 | A. flavus | | Air hospital | NEM, Paris, France | AY017536 | |
| FLA | 15 | A. flavus | | Sputum | NEM, Paris, France | AY017536 | |
| FLA | 16 | A. flavus | | Sputum | NEM, Paris, France | AY017536 | |
| FLA | 18 | A. flavus | Flavi | Air hospital | NEM, Paris, France | EF661492 | |
| FLA | 19 | A. flavus | | Nasopharyngeal lavage | NEM, Paris, France | EF661492 | |
| FLA | 25 | A. flavus | | Bronchoalveolar lavage | NEM, Paris, France | EF661492 | |
| FLA | 22 | A. flavus | | Bronchoalveolar lavage | NEM, Paris, France | EF661492 | |
| FLA | 30 | A. flavus | | Nasopharyngeal lavage | NEM, Paris, France | EF661492 | |
| FLA | 31 | A. flavus | | Sputum | NEM, Paris, France | EF661492 | |
| ASPSP SL | 03 | A. parvislerotigenus | | Bronchotracheal aspiration | SL, Paris, France | EF203130 | EF202077 |
| FLA | 17 | A. tamarii | | Bronchoalveolar lavage | NEM, Paris, France | AY0175410 | EU021686 |
| FLA | 29 | A. tamarii | | Bronchoalveolar lavage | NEM, Paris, France | AY0175410 | EU021686 |
| CNM | CM3227 | A. fumiaffinitis | Fumigati | Bronchoalveolar lavage | CNM, Madrid, Spain | * | * |
| CNM | CM2280 | A. fumiaffinitis | | Sputum | CNM, Madrid, Spain | * | * |
| ASPSP CO | 01 | A. fumigatus | | Bronchoalveolar lavage | CO, Paris, France | AY048754 | |
| ASPSP | 06 | A. fumigatus | | Air hospital | NEM, Paris, France | AY048754 | |
| FUM | 01 | A. fumigatus | | Sputum | NEM, Paris, France | AY048754 | |
| FUM | 02 | A. fumigatus | | Sputum | NEM, Paris, France | AY048754 | |
| FUM | 03 | A. fumigatus | | Sputum | NEM, Paris, France | AY048754 | |
| FUM | 05 | A. fumigatus | | Sputum | NEM, Paris, France | AY048754 | |
| FUM | 06 | A. fumigatus | | Sputum | NEM, Paris, France | AY048754 | |
| FUM | 07 | A. fumigatus | | Sputum | NEM, Paris, France | AY048754 | |
| FUM | 09 | A. fumigatus | | Sputum | NEM, Paris, France | AY048754 | |
| FUM | 11 | A. fumigatus | | Sputum | NEM, Paris, France | AY048754 | |
| FUM | 12 | A. fumigatus | | Sputum | NEM, Paris, France | AY048754 | |
| FUM | 14 | A. fumigatus | | Sputum | NEM, Paris, France | AY048754 | |
| FUM | 15 | A. fumigatus | | Sputum | NEM, Paris, France | AY048754 | |
| FUM | 16 | A. fumigatus | | Sputum | NEM, Paris, France | AY048754 | |
| FUM | 18 | A. fumigatus | | Sputum | NEM, Paris, France | AY048754 | |
| FUM | 19 | A. fumigatus | | Sputum | NEM, Paris, France | AY048754 | |
| FUM | 23 | A. fumigatus | | Sputum | NEM, Paris, France | AY048754 | |
| FUM | 24 | A. fumigatus | | Sputum | NEM, Paris, France | AY048754 | |
| FUM | 28 | A. fumigatus | | Sputum | NEM, Paris, France | AY048754 | |
| FUM | 29 | A. fumigatus | | Sputum | NEM, Paris, France | AY048754 | |
| FUM | 30 | A. fumigatus | | Skin | NEM, Paris, France | AY048754 | |
| FUM | 31 | A. fumigatus | | Sputum | NEM, Paris, France | AY048754 | |
| FUM | 32 | A. fumigatus | | Sputum | NEM, Paris, France | AY048754 | |
| FUM | 33 | A. fumigatus | | Sputum | NEM, Paris, France | AY048754 | |
| FUM | 34 | A. fumigatus | | Sputum | NEM, Paris, France | AY048754 | |
| FUM | 35 | A. fumigatus | | Bronchoalveolar lavage | NEM, Paris, France | AY048754 | |
| FUM | 36 | A. fumigatus | | Sputum | NEM, Paris, France | AY048754 | |
| FUM | 37 | A. fumigatus | | Bronchoalveolar lavage | NEM, Paris, France | AY048754 | |
| FUM | 38 | A. fumigatus | | Sputum | NEM, Paris, France | AY048754 | |
| FUM | 40 | A. fumigatus | | Sputum | NEM, Paris, France | AY048754 | |
| FUM | 41 | A. fumigatus | | Bronchoalveolar lavage | NEM, Paris, France | AY048754 | |
| FUM | 43 | A. fumigatus | | Sputum | NEM, Paris, France | AY048754 | |
| FUM | 44 | A. fumigatus | | Sputum | NEM, Paris, France | AY048754 | |
| FUM | 45 | A. fumigatus | | Bronchoalveolar lavage | NEM, Paris, France | AY048754 | |
| FUM | 46 | A. fumigatus | | Sputum | NEM, Paris, France | AY048754 | |
| FUM | 47 | A. fumigatus | | Air hospital | NEM, Paris, France | AY048754 | |
| FUM | 48 | A. fumigatus | | Sputum | NEM, Paris, France | AY048754 | |
| FUM | 49 | A. fumigatus | | Bronchoalveolar lavage | NEM, Paris, France | AY048754 | |
| FUM | 50 | A. fumigatus | | Sputum | NEM, Paris, France | AY048754 | |
| FUM | 51 | A. fumigatus | | Sputum | NEM, Paris, France | AY048754 | |
| FUM | 52 | A. fumigatus | | Sputum | NEM, Paris, France | AY048754 | |
| FUM | 53 | A. fumigatus | | Sputum | NEM, Paris, France | AY048754 | |
| FUM | 54 | A. fumigatus | | Sputum | NEM, Paris, France | AY048754 | |
| FUM | 55 | A. fumigatus | | Bronchoalveolar lavage | NEM, Paris, France | AY048754 | |
| FUM | 56 | A. fumigatus | | Sputum | NEM, Paris, France | AY048754 | |
| FUM | 57 | A. fumigatus | | Skin | NEM, Paris, France | AY048754 | |
| FUM | 58 | A. fumigatus | | Sputum | NEM, Paris, France | AY048754 | |
| FUM | 59 | A. fumigatus | | Sputum | NEM, Paris, France | AY048754 | |
| FUM | 60 | A. fumigatus | | Bronchoalveolar lavage | NEM, Paris, France | AY048754 | |
| ASPSP SL | 05 | A. fumigatus | | Bronchotracheal aspiration | SL, Paris, France | AY048754 | |
| CNM | CM4063 | A. fumisynematus | | Bronchoalveolar aspirate | CNM, Madrid, Spain | * | * |

TABLE 11-continued

| Isolates number | | Specie | Section | Source | Geographical origin | GenBank Identification number (betatubulin) | GenBank Identification number (calmodulin) |
|---|---|---|---|---|---|---|---|
| CNM | CM3303 | A. hiratsukae | | Skin | CNM, Madrid, Spain | * | * |
| CNM | CM3305 | A. hiratsukae | | Skin | CNM, Madrid, Spain | * | * |
| CNM | CM1290 | A. lentulus | | Sputum | CNM, Madrid, Spain | * | * |
| CNM | CM3364 | A. lentulus | | Bronchoalveolar lavage | CNM, Madrid, Spain | * | * |
| CNM | CM3537 | A. lentulus | | Sputum | CNM, Madrid, Spain | * | * |
| CNM | CM3583 | A. lentulus | | Sputum | CNM, Madrid, Spain | * | * |
| CNM | CM3599 | A. lentulus | | Sputum | CNM, Madrid, Spain | * | * |
| CNM | CM3134 | A. lentulus | | Sputum | CNM, Madrid, Spain | * | * |
| CNM | CM3538 | A. lentulus | | Sputum | CNM, Madrid, Spain | * | * |
| CNM | CM4518 | A. viridinutans | | Nail | CNM, Madrid, Spain | * | * |
| CNM | CM3147 | A. viridinutans | | Oropharyngeal exsudate | CNM, Madrid, Spain | * | * |
| FIS | 01 | N. fischeri | | Bronchoalveolar lavage | NEM, Paris, France | AY870729 | |
| CNM | CM2270 | N. pseudofischeri | | Sputum | CNM, Madrid, Spain | * | * |
| CNM | CM4060 | N. pseudofischeri | | Sputum | CNM, Madrid, Spain | * | * |
| CNM | CM3914 | N. pseudofischeri | | Sputum | CNM, Madrid, Spain | * | * |
| ASPSP | 25 | N. pseudofischeri | | Sputum | NEM, Paris, France | EF669823 | |
| PSE | 01 | N. pseudofischeri | | Bronchoalveolar lavage | NEM, Paris, France | EF669823 | |
| CNM | CM4635 | N. udagawae | | Sputum | CNM, Madrid, Spain | * | * |
| NID | 06 | A. nidulans | | Bronchoalveolar lavage | NEM, Paris, France | AY573547 | EF652400 |
| NID | 10 | A. nidulans | | Bronchoalveolar lavage | NEM, Paris, France | AY573547 | EF652400 |
| NID | 13 | A. nidulans | | Sputum | NEM, Paris, France | AY573547 | EF652400 |
| ASPSP SL | 06 | A. nidulans | | Sputum | SL, Paris, France | AY573547 | EF652400 |
| ASPSP | 04 | A. sydowii | | Air hospital | NEM, Paris, France | EU907905 | |
| ASPSP | 27 | A. sydowii | | Air hospital | NEM, Paris, France | EU907905 | |
| SYD | 04 | A. sydowii | | Sputum | NEM, Paris, France | EU907905 | |
| SYD | 01 | A. sydowii | Nidulantes | Sputum | NEM, Paris, France | EU907905 | |
| SYD | 02 | A. sydowii | | Sputum | NEM, Paris, France | EU907905 | |
| SYD | 03 | A. sydowii | | Sputum | NEM, Paris, France | EU907905 | |
| ASPSP SL | 01 | A. sydowii | | Bronchotracheal aspiration | SL, Paris, France | EU907905 | |
| ASPSP | 02 | A. versicolor | | Air hospital | NEM, Paris, France | EF652291 | EF652379 |
| VER | 01 | A. versicolor | | Sputum | NEM, Paris, France | EF652291 | EF652379 |
| VER | 03 | A. versicolor | | Sputum | NEM, Paris, France | EF652291 | EF652379 |
| NID | 08 | E. quadrilineata | | Bronchoalveolar lavage | NEM, Paris, France | EF652288 | EF652376 |
| ASPSP | 03 | A. foetidus | | Air hospital | NEM, Paris, France | AY585533 | AM419749 |
| NIG | 15 | A. foetidus | | Skin | NEM, Paris, France | AY585533 | AM419749 |
| NIG | 01 | A. niger | | Nasopharyngeal lavage | NEM, Paris, France | AY820002 | |
| NIG | 03 | A. niger | | Air hospital | NEM, Paris, France | AY820002 | |
| NIG | 04 | A. niger | | Sputum | NEM, Paris, France | AY820002 | |
| NIG | 05 | A. niger | Nigri | Air hospital | NEM, Paris, France | AY820002 | |
| NIG | 06 | A. niger | | Sputum | NEM, Paris, France | AY820002 | |
| NIG | 07 | A. niger | | Sputum | NEM, Paris, France | AY820002 | |
| NIG | 16 | A. niger | | Sputum | NEM, Paris, France | AY820002 | |
| NIG | 17 | A. niger | | Sputum | NEM, Paris, France | AY820002 | |
| NIG | 25 | A. niger | | Air hospital | NEM, Paris, France | AY820002 | |
| NIG | 11 | A. tubengensis | | Bronchoalveolar lavage | NEM, Paris, France | AY820009 | EF661150 |
| TER | 01 | A. terreus | | Skin | NEM, Paris, France | EF669520 | |
| TER | 02 | A. terreus | | Sputum | NEM, Paris, France | EF669520 | |
| TER | 05 | A. terreus | | Sputum | NEM, Paris, France | EF669520 | |
| TER | 06 | A. terreus | Terrei | Sputum | NEM, Paris, France | EF669520 | |
| TER | 07 | A. terreus | | Sputum | NEM, Paris, France | EF669520 | |
| TER | 08 | A. terreus | | Sputum | NEM, Paris, France | EF669520 | |
| TER | 10 | A. terreus | | Sputum | NEM, Paris, France | EF669520 | |
| TER | 11 | A. terreus | | Sputum | NEM, Paris, France | EF669520 | |
| ASPSP | 01 | A. calidoustus | | Air hospital | NEM, Paris, France | EF591730 | EF591716 |
| UST | 11 | A. calidoustus | | Sputum | NEM, Paris, France | EF591730 | EF591716 |
| CNRMA | F2-25 | A. calidoustus | | Bronchoalveolar lavage | SL, Paris, France | EF591730 | EF591716 |
| CNRMA | F5-22 | A. calidoustus | | Sputum | SL, Paris, France | EF591730 | EF591716 |
| CNRMA | F6-60 | A. calidoustus | | Bronchoalveolar lavage | SL, Paris, France | EF591730 | EF591716 |
| CNRMA | F6-64 | A. calidoustus | | Sputum | SL, Paris, France | EF591730 | EF591716 |
| CNRMA | F6-66 | A. calidoustus | Usti | Sputum | SL, Paris, France | EF591730 | EF591716 |
| CNRMA | F7-8 | A. calidoustus | | Sputum | SL, Paris, France | EF591730 | EF591716 |
| CNRMA | F7-13 | A. calidoustus | | Air hospital | SL, Paris, France | EF591730 | EF591716 |
| CNRMA | F7-15 | A. calidoustus | | Air hospital | SL, Paris, France | EF591730 | EF591716 |
| CNRMA | F7-17 | A. calidoustus | | Air hospital | SL, Paris, France | EF591730 | EF591716 |
| CNRMA | F1-79 | A. insuetus | | Bronchoalveolar lavage | SL, Paris, France | EU076372 | |
| ASPSP | 26 | A. pseudodeflectus | | Air hospital | NEM, Paris, France | EF591732 | |

*refer to Alcazar-Fuoli et al., AAC 2008

Tableau 12 gives results concerning the identification of *Aspergilli* by MALDI-TOF-MS based on the presence≧66% of the peak of the first match of the database specie and>10% difference between the first and the second match, after the first and the second passage The panel of reference strains which were included in the study, was concordant with the distribution of *Aspergillus* species isolated in patients. In addition, the recently-described species which cannot be identified using traditional phenotypic approaches (non-*A. fumigatus* species of the sec-

| Section (number of strains) | Species | Number of strains | Concordance between MALDI-TOF-MS and MLS with a single passage (%) | | Concordance between MALDI-TOF-MS and MLS with two passages (%) | |
|---|---|---|---|---|---|---|
| | | | Early spores | Late spores | Early spores | Late spores |
| Fumigati (n = 71) | *A. fumigatus* | 50 | 44/50 (88%) | 44/50 (88%) | 47/50 (94%) | 48/50 (96%)* |
| | *A. lentulus* | 7 | 21/21 (100%) | | / | |
| | *Neosartorya pseudofischeri* | 5 | | | | |
| | *N. fischeri* | 1 | | | | |
| | *A. fumigatiaffinis* | 2 | | | | |
| | *A. fumisynnematus* | 1 | | | | |
| | *A. viridinutans* | 2 | | | | |
| | *N. udagawae* | 1 | | | | |
| | *N. hiratsukae* | 2 | | | | |
| Flavi (n = 16) | *A. flavus* | 13 | 12/16 (75%) | | 16/16 (100%) | |
| | *A. tamari* | 2 | | | | |
| | *A. parvisclerotigenus* | 1 | | | | |
| Terrei (n = 8) | *A. terreus* | 8 | 8/8 (100%) | | / | |
| Nigri (n = 12) | *A. niger* | 9 | 10/12 (83.3%) | | 12/12 (100%) | |
| | *A. tubengensis* | 1 | | | | |
| | *A. foetidus* | 2 | | | | |
| Nidulantes (n = 15) | *Emericella nidulans* | 4 | 13/15 (86.6%) | | 15/15 (100%) | |
| | *E. quadrilineata* | 1 | | | | |
| | *A. sydowii* | 7 | | | | |
| | *A. versicolor* | 3 | | | | |
| Usti (n = 13) | *A. calidoustus* | 11 | 12/13 (92.3%) | | 13/13 (100%) | |
| | *A. pseudodeflectus* | 1 | | | | |
| | *A. insuetus* | 1 | | | | |
| Circumdati (n = 1) | *A. ochraceus* | 1 | 1/1 (100%) | | / | |
| Total | 24 | 136 | 121/136 (89%) | | 134/136 (98.4%) | |

*1 non-sporulating *A. fumigatus* strain non identified and 1 poorly-sporulating *A. fumigatus* strain identified as *A. fumigatus* (50% of matching peaks) with 10% difference with the second match after 1 month of culture For each isolate, all peaks with intensity >0.01 were retained and were compared with that of the specific peaks of each reference strain included in the database using the BGP-database software, taking into account a possible error of +/−10 m/z value. Then the percentage of common peaks were obtained. Only the first and second best matches were retained. Acceptable identification of a tested strain corresponds to the species having ≧66% of common peaks with the reference strains in the database. A difference of at least 10% between the first and the second match is required.

Using the database of the invention, identification was correct in 121 of 136 isolates (89%) after the first passage and in 134/136 (98.4%) after the second passage. In table, results of MALDI-TOF-MS identification are presented for each section. No strains was misidentified, leading a specificity of 100%.

Conclusion

These results demonstrate that the MALDI-TOF database developed and validated according to the invention allows precise identification of an extensive number of *Aspergillus* species currently isolated in clinical settings, including the recently described species, such as *A. lentulus*, *N. pseudofischeri*, *A. calidoustus*, *E. quadrilineata* (sensitivity: 98.4%, specificity: 100%).

The database includes the reference spectra from early-spores and late-spores for each species but 2. This originality allows identification of *Aspergillus* isolates whatever the maturity of the tested isolate.

tion *Fumigati*, *E. quadrilineata* in the Section Nidulantes, and *A. insuetus* or *A. pseudodeflectus* in the section Usti), have been studied and included.

The invention claimed is:

1. A method for identifying a germ strain isolated from a clinical sample, at least one of the species and subspecies level, using MALDI-TOF-MS analysis comprising a step of classifying the germ in a group before performing the MALDI-TOF-MS analysis, wherein said analysis comprises retaining in the spectrum of a tested strain, peaks having, compared to a peak with the highest intensity arbitrary set up to 1, a relative intensity higher than 0.05.

2. The method of claim 1, wherein the classification step is based on at least one of growth conditions, a characteristic of colonies, morphology of bacteria upon microscopic examination, gram stain and phenotypic tests.

3. The method of claim 1, comprising performing the MALDI-TOF-MS technique on whole intact cells or on protein extracts obtained after lysis or corresponding to a fraction of cellular components.

4. The method of claim 1, comprising adding a benzoic acid derivative as matrix medium to isolated colonies before performing the MALDI-TOF-MS analysis, said benzoic acid derivative being advantageously selected in the group comprising DHB, and optionally further contains sinnapic acid fior the identification of *Mycobacterium*.

5. The method of claim 1, wherein each spectrum is the sum of at least 300 laser shots, coming from different regions containing the strain to be analyzed, said spectrum being analyzed, in a range of m/z from 500 to 50 000.

6. The method of claim 5, comprising using at least 1000 laser shots.

7. The method of claim 6, comprising using at least 2000 laser shots.

8. The method of claim 5, wherein said spectrum is analyzed in a range of m/z from 500 to 20000.

9. The method of claim 8, wherein said spectrum is analyzed in a range of m/z from 2000 to 20000.

10. The method of claim 1, wherein the strain to be identified is selected in the group comprising bacteria.

11. The method of claim 10, wherein the bacteria is a coagulase-negative *Staphylococcus*.

12. The method of claim 10, wherein the bacteria is a non fermenting Gram negative *bacilli*.

13. The method of claim 1, wherein the strain to be identified is selected in the group comprising yeasts.

14. The method of claim 1, wherein the strain to be identified is selected in the group comprising molds, such as filamentous fungi.

15. A method for identifying a germ strain isolated from a clinical sample, at least one of the species and subspecies level, using MALDI-TOF-MS analysis comprising a step of classifying the germ in a group before performing the MALDI-TOF-MS analysis, wherein said analysis comprises the step of comparing the spectrum profile of strains to be identified obtained by performing said MALDI-TOF-MS analysis with a database containing the characteristic MALDI-TOF-MS spectra of strains representative of the species or subspecies of the group of germs to which belongs the strain to be identified, said database containing for each representative strain, peaks having, compared to the peak with the highest intensity arbitrary set up to 1, a relative intensity higher than 0.1.

16. The method of claim 15, wherein said database contains for each representative strain, peaks having, compared to the peak with the highest intensity arbitrary set up to 1, a relative intensity higher than 0.05.

17. The method of claim 16, wherein said database contains for each representative strain, peaks having, compared to the peak with the highest intensity arbitrary set up to 1, a relative intensity higher than 0.1.

18. Databases consisting of peaks selected in the spectra obtained by MALDI-TOF-MS analysis of representative strains of species or subspecies, said databases being obtained
    using a set of strains, each species or subspecies being represented by one or several strains, and
    recording the spectrum of each strain of such group by using MALDI-TOF-MS and retaining the peaks with a relative intensity above 0.01 for fungi identification, and above 0.02 for other germs, which are present in at least 2 sub-culture.

19. The databases of claim 18, wherein, for each representative strain, the selected peaks have compared to the peak with the highest intensity arbitrary set up to 1, a relative intensity higher than 0.05.

20. The databases of claim 18, wherein, for each representative strain, the selected peaks have compared to the peak with the highest intensity arbitrary set up to 1, a relative intensity higher than 0.1.

* * * * *